USO05812983A

United States Patent [19]

Kumagai

[11] Patent Number: 5,812,983

[45] Date of Patent: Sep. 22, 1998

[54] COMPUTED MEDICAL FILE AND CHART SYSTEM

[76] Inventor: Yasuo Kumagai, 344-29, Imaichi, Imach8i-shi, Tochigi-ken, 321-132, Japan

[21] Appl. No.: 510,665

[22] Filed: Aug. 3, 1995

[51] Int. Cl.⁶ .................. G06F 159/00; G06F 17/06
[52] U.S. Cl. .................. 705/3; 705/2; 707/503; 364/577; 364/723; 395/440
[58] Field of Search .................. 395/202, 203, 395/764, 765, 140, 142, 143; 364/723, 577; 705/2, 3; 707/503, 504; 345/440, 442, 443

[56] References Cited

U.S. PATENT DOCUMENTS

| 3,789,203 | 1/1974 | Catherall et al. | 364/723 |
|---|---|---|---|
| 3,996,456 | 12/1976 | Hoover | 364/807 |
| 4,446,529 | 5/1984 | Strolle | 364/723 |
| 4,752,826 | 6/1988 | Barnett | 348/192 |
| 4,878,175 | 10/1989 | Norden-Paul et al. | 395/202 |
| 5,199,439 | 4/1993 | Zimmerman et al. | 128/670 |
| 5,235,510 | 8/1993 | Yamada et al. | 128/653.1 |
| 5,247,611 | 9/1993 | Norden-Paul et al. | 395/765 |
| 5,253,362 | 10/1993 | Nolan et al. | 395/601 |
| 5,257,355 | 10/1993 | Akamatsu | 395/142 |
| 5,258,938 | 11/1993 | Akamatsu | 364/723 |
| 5,262,943 | 11/1993 | Thibado et al. | 128/630 |
| 5,303,146 | 4/1994 | Ammirato et al. | 395/764 |
| 5,307,263 | 4/1994 | Brown | 128/668 |
| 5,307,455 | 4/1994 | Higgins et al. | 395/140 |
| 5,325,478 | 6/1994 | Shelton et al. | 395/768 |
| 5,337,405 | 8/1994 | Lindauer et al. | 395/764 |
| 5,581,677 | 12/1996 | Myers et al. | 395/140 |
| 5,610,833 | 3/1997 | Chang et al. | 364/491 |

FOREIGN PATENT DOCUMENTS

| 0 643 360 | 9/1994 | European Pat. Off. | G06F 19/00 |
|---|---|---|---|
| 2 260 632 | 4/1993 | United Kingdom | G06F 3/14 |

OTHER PUBLICATIONS

"The Computerized Patient Record", Scott Wallace, pp. 67–75, *Byte*, May 1994.

*Medical Records, Medical Education, and Patient Care*, Lawrence L. Weed, M.D., The Press of Case Western Reserve University, Year Book Medical Publishers, Inc., pp. 1–83.

PTC International Publication No. WO 93/24896, Publication Date: 9 Dec. 1993, Hewlett–Packard Co.

PTC International Publication No. WO 92/06437, Publication Date: 16 Apr. 1992, Hewlett–Pakc.

*Graphical Representation of Medical Information in the Visual Chart*, Harold I. Lett and John W. Loonsk, M.D., Publ. Date Nov. 6, 1994.

Yamazaki's report, 13th JCMI (Nov. 1993). 2–E–17, 13th JCMI (Nov. 1993).

Grabow, et al: "Computer–Controlled Documentation of Intensive Care and Anaesthesia Data". Intensiv–Notfall behandl 18(1), pp. 34–39 Dialog File 5, Acc#10410658, 1993.

*Primary Examiner*—David R. Hudspeth
*Assistant Examiner*—Joseph Thomas
*Attorney, Agent, or Firm*—Lane, Aitken & McCann

[57] ABSTRACT

A method for integrating and displaying medical data in which a computer program links a flow sheet of a medical record to medical charts. The flow sheet has a standardized time scale in the rows and a group of data items in the columns. The program determines the position of a cursor in the flow sheet, and interpolates or erases data in cells of the flowsheet as appropriate. Each empty data cell between cells containing real data is interpolated according to a predetermined formula. The interpolation method can be one in which an average of the preceding cell and the subsequent cell are recalculated up to several hundred times. Another interpolation method involves the use of a gradient, row values and an intercept. The resulting medical charts are designed so that therapeutic data and clinical data are simultaneously displayed on the same chart with the same time scale. The system can be connected to a client server system of a computer network. The system allows the comparison of regularly collected data of many patients because it has a standardized time scale and data interpolated by an appropriate formula.

22 Claims, 27 Drawing Sheets patient's I.D.
patient's name
93/12/19
93/12/19 ~ 12/25   1

| DATE | WK | data item | data item 2 |
|---|---|---|---|
|  |  |  |  |
| 93/12/19 ~ 12/25 | 1 |  |  |
| 12/26 ~ 01/01 | 2 |  |  |
| 01/02 ~ 01/08 | 3 |  |  |
| 01/09 ~ 01/15 | 4 |  |  |
| 01/16 ~ 01/22 | 5 |  |  |
| 01/23 ~ 01/29 | 6 |  |  |
| 01/30 ~ 02/05 | 7 |  |  |
| 02/06 ~ 02/12 | 8 |  |  |
| 02/13 ~ 02/19 | 9 |  |  |
| 02/20 ~ 02/26 | 10 |  |  |
| 02/27 ~ 03/05 | 11 |  |  |
| 03/06 ~ 03/12 | 12 |  |  |
| 03/13 ~ 03/19 | 13 |  |  |
| 03/20 ~ 03/26 | 14 |  |  |
| 03/27 ~ 04/02 | 15 |  |  |
| 04/03 ~ 04/09 | 16 |  |  |
| 04/10 ~ 04/16 | 17 |  |  |
| 04/17 ~ 04/23 | 18 |  |  |
| 04/24 ~ 04/30 | 19 |  |  |
| 05/01 ~ 05/07 | 20 |  |  |
| 05/08 ~ 05/14 | 21 |  |  |
| 05/15 ~ 05/21 | 22 |  |  |
| 05/22 ~ 05/28 | 23 |  |  |
| 05/29 ~ 06/04 | 24 |  |  |
| 06/05 ~ 06/11 | 25 |  |  |
| 06/12 ~ 06/18 | 26 |  |  |
| 06/19 ~ 06/25 | 27 |  |  |

FIG.2A patient's I.D.
patient's name
93/12/19
12/20 mon 1

| DATE | WK | HSP | data item | data item 2 |
|---|---|---|---|---|
|  |  |  |  |  |
| 93/12/19 | sun | 1 |  |  |
| 12/20 | mon | 2 |  |  |
| 12/21 | tue | 3 |  |  |
| 12/22 | wed | 4 |  |  |
| 12/23 | thr | 5 |  |  |
| 12/24 | fri | 6 |  |  |
| 12/25 | sat | 7 |  |  |
| 12/26 | sun | 8 |  |  |
| 12/27 | mon | 9 |  |  |
| 12/28 | tue | 10 |  |  |
| 12/29 | wed | 11 |  |  |
| 12/30 | thr | 12 |  |  |
| 12/31 | fri | 13 |  |  |
| 01/02 | sat | 14 |  |  |
| 01/03 | sun | 15 |  |  |
| 01/04 | mon | 16 |  |  |
| 01/05 | tue | 17 |  |  |
| 01/06 | wed | 18 |  |  |
| 01/07 | thr | 19 |  | . |
| 01/08 | fri | 20 |  |  |
| 01/09 | sat | 21 |  |  |
| 01/10 | sun | 22 |  |  |
| 01/11 | mon | 23 |  |  |
| 01/12 | tue | 24 |  |  |
| 01/13 | wed | 25 |  |  |
| 01/14 | thr | 26 |  |  |
| 01/15 | fri | 27 |  |  |

FIG.2B patient's I.D.
patient's name
93/12/26

| DATE | HSP | TRIM | data item | data item 2 |
|---|---|---|---|---|
| 93/12/26 | 1 | M | | |
| | | E | | |
| | | N | | |
| 93/12/27 | 2 | M | | |
| | | E | | |
| | | N | | |
| 93/12/28 | 3 | M | | |
| | | E | | |
| | | N | | |
| 93/12/29 | 4 | M | | |
| | | E | | |
| | | N | | |
| 93/12/30 | 5 | M | | |
| | | E | | |
| | | N | | |
| 93/12/31 | 6 | M | | |
| | | E | | |
| | | N | | |
| 94/01/01 | 7 | M | | |
| | | E | | |
| | | N | | |
| 94/01/02 | 8 | M | | |
| | | E | | |
| | | N | | |
| 94/01/03 | 9 | M | | |
| | | E | | |
| | | N | | |

FIG.2C patient's I.D.
patient's name
93/12/26

| DATE | HSP | HOUR | data item1 | data item |
|---|---|---|---|---|
| | | | | |
| 93/12/26 | 1 | 1 | | |
| 93/12/26 | 1 | 2 | | |
| 93/12/26 | 1 | 3 | | |
| 93/12/26 | 1 | 4 | | |
| 93/12/26 | 1 | 5 | | |
| 93/12/26 | 1 | 6 | | |
| 93/12/26 | 1 | 7 | | |
| 93/12/26 | 1 | 8 | | |
| 93/12/26 | 1 | 9 | | |
| 93/12/26 | 1 | 10 | | |
| 93/12/26 | 1 | 11 | | |
| 93/12/26 | 1 | 12 | | |
| 93/12/26 | 1 | 13 | | |
| 93/12/26 | 1 | 14 | | |
| 93/12/26 | 1 | 15 | | |
| 93/12/26 | 1 | 16 | | |
| 93/12/26 | 1 | 17 | | |
| 93/12/26 | 1 | 18 | | |
| 93/12/26 | 1 | 19 | | |
| 93/12/26 | 1 | 20 | | |
| 93/12/26 | 1 | 21 | | |
| 93/12/26 | 1 | 22 | | |
| 93/12/26 | 1 | 23 | | |
| 93/12/26 | 1 | 24 | | |
| 93/12/27 | 2 | 1 | | |
| 93/12/27 | 2 | 2 | | |
| 93/12/27 | 2 | 3 | | |

FIG.2D patient's name

00/01/01 ****

| DATE | HSP | BS 7:00 | BS 21:00 | Hb-Alc | UV | diet | Daonil |
|---|---|---|---|---|---|---|---|
| | | | | | | | |
| 93/10/25 | 1 | | | 11.1 | | | |
| 93/10/26 | 2 | | | | 2000 | 1600 | |
| 93/10/27 | 3 | | | | 1800 | | |
| 93/10/28 | 4 | 295.9 | | | 1600 | | |
| 93/10/29 | 5 | | | | 1250 | | |
| 93/10/30 | 6 | 283.3 | 383.7 | | 1700 | | |
| 93/10/31 | 7 | | | | | | |
| 93/11/01 | 8 | | | | 1350 | | |
| 93/11/02 | 9 | 260.4 | 366.3 | 10.5 | | | |
| 93/11/03 | 10 | | | | 1100 | | |
| 93/11/04 | 11 | | | | | | |
| 93/11/05 | 12 | | | | 1000 | | |
| 93/11/06 | 13 | | | | 1200 | | |
| 93/11/07 | 14 | | | | 1150 | | |
| 93/11/08 | 15 | 221.6 | 284.1 | | 950 | | |

FIG.3A patient's name

| 148 | 00/01/01 | +B147+ | (+C147+C149)/2 | (+D147+D149)/2 | (+E147+E149)/2 | | | +G147 | +H147 |
|---|---|---|---|---|---|---|---|---|---|
| 149 | DATE | HSP D | BS 7:00 | BS 21:00 | Hb-A1c | UV | diet | | Daonil |
| 150 | | | | | | | | | |
| 151 | 93/10/25 | 1 | | | | | | | |
| 152 | 93/10/26 | 2 | | | | 2000 | 1600 | | |
| 153 | 93/10/27 | 3 | | | (+E151+D153)/2 | 1800 | +G153 | | |
| 154 | 93/10/28 | 4 | 295.9 | | (+E152+D154)/2 | 1600 | +G154 | | |
| 155 | 93/10/29 | 5 | (+C154+C156)/2 | | (+E153+D155)/2 | 1250 | +G155 | | |
| 156 | 93/10/30 | 6 | 283.3 | 383.7 | (+E154+D156)/2 | 1700 | +G156 | | |
| 157 | 93/10/31 | 7 | (+C156+C158)/2 | (+D156+D158)/2 | (+E155+D157)/2 | | +G157 | | |
| 158 | 93/11/01 | 8 | (+C157+C159)/2 | (+D157+D159)/2 | (+E156+D158)/2 | 1350 | +G158 | | |
| 159 | 93/11/02 | 9 | 260.4 | 366.3 | (+E157+D159)/2 | | +G159 | | |
| 160 | 93/11/03 | 10 | (+C159+C161)/2 | (+D159+D161)/2 | (+E159+D161)/2 | 1100 | +G160 | | |
| 161 | 93/11/04 | 11 | (+C160+C162)/2 | (+D160+D162)/2 | (+E160+D162)/2 | | +G161 | | |
| 162 | 93/11/05 | 12 | (+C161+C163)/2 | (+D161+D163)/2 | (+E161+E163)/2 | 1000 | +G162 | | |
| 163 | 93/11/06 | 13 | (+C162+C164)/2 | (+D162+D164)/2 | (+E162+D164)/2 | 1200 | +G163 | | |
| 164 | 93/11/07 | 14 | (+C163+C165)/2 | (+D163+D165)/2 | (+E163+D165)/2 | 1150 | +G164 | | |
| 165 | 93/11/08 | 15 | 221.6 | 284.1 | (+E164+D166)/2 | 950 | | | |

FIG.3B

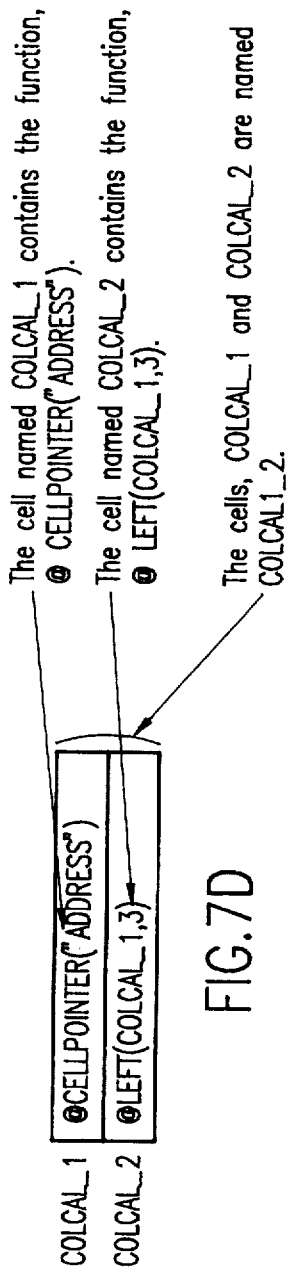

The cell named COLCAL_1 contains the function,
@CELLPOINTER("ADDRESS").

The cell named COLCAL_2 contains the function,
@LEFT(COLCAL_1,3).

The cells, COLCAL_1 and COLCAL_2 are named COLCAL1_2.

FIG.7D

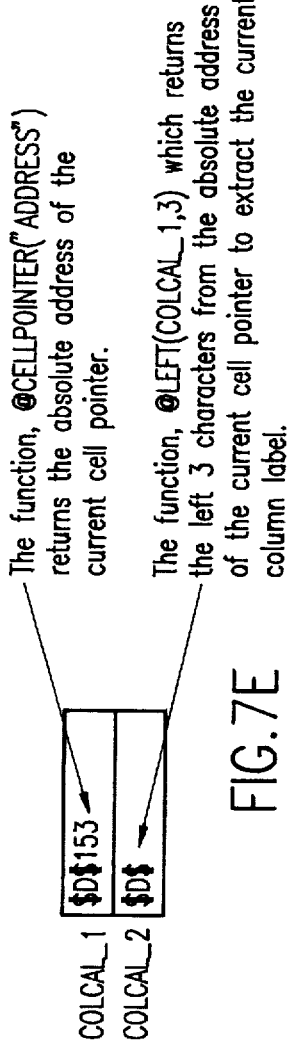

The function, @CELLPOINTER("ADDRESS") returns the absolute address of the current cell pointer.

The function, @LEFT(COLCAL_1,3) which returns the left 3 characters from the absolute address of the current cell pointer to extract the current column label.

FIG.7E

| 91 | {recalc COLCAL1_2} |
| 92 | {let HOKAN_3,COLCAL_2&+"148":value} |
| 93 | {menu}c |
| 94 | $D$148 |
| 95 | ~HOKAN~ |

The cell of step 94 is named HOKAN_3 and locally unprotected.

FIG.7F

91. The cells, COLCAL1_2 are recalculated.
92. The current column label in COLCAL_2 is combined with 148, and the result is written to HOKAN_3 which is the cell name of step 94 of the program list. The cell is locally unprotected.
93 to 95. The formula written in the row 148 of the current column is copied to the area named HOKAN. This macro command could be same as {menu}c$D$148~HOKAN~. In this case, the program has to rewrite $D$148 according to the current column.

directory table

|           | no 1         | no 2           | no 3          | no 4 |
|-----------|--------------|----------------|---------------|------|
| DIRECTRY  | C:\LABO      | I:\NURSE       | I:\NURSE      |      |
| FILE_NAME | LABO_DAT.DBF | PT_DATA.DBF    | DRUG.DBF      |      |
| CONDITION | COND_1       | COND_1         | COND_1        |      |
| OUTPUT    | OUT 1        | OUT 2          | OUT 3         |      |

FIG.11B date calculation table

| DAY_CTR    | 3                              |
|------------|--------------------------------|
| FIRST_DATE | @DATE(93,10,25)                |
| START_DATE | 93/10/30                       |
| DATA_DATE  | START_DATE+DAY_CTR             |
| CHA_DATE   | 93/11/02                       |
| TODAY      | @INT(@NOW)                     |
| DATE_DIF   | @DATEDIF(FIRST_DATE,DATA_DATE,"d") |

FIG.11C

| CPK \ HSP DAY | PMDM without interstitial pneumonia | | | | | |
|---|---|---|---|---|---|---|
| | patient 1 | patient 2 | patient 3 | patient 4 | patient 5 | patient 6 |
| 1 | | | | | | |
| 2 | 1943 | 1596 | | 2818 | 354 | |
| 3 | | | | | | |
| 4 | | | 7565 | | | |
| 5 | | | | | | |
| 6 | | | | | | |
| 7 | | | 9075 | | | |
| 8 | | | | 2246 | | |
| 9 | | 1993 | | | | 339 |
| 10 | | | | | 250 | |
| 11 | | | | 1550 | | |
| 12 | | | 6573 | | | |
| 13 | | | | | | |
| 14 | | 1107 | | | | |
| 15 | | | | 739 | | 158 |
| 16 | | | | | 98 | |
| 17 | 1568 | | | | | |
| 18 | | | 1750 | 219 | | |
| 19 | | | | | | |
| 20 | | | | | | |
| 21 | | 981 | | | | |
| 22 | | | | 136 | | 65 |
| 23 | | | | | | |
| 24 | 229 | | | | | |

FIG.12A

| | 100 | 100 |
|---|---|---|
| +$TOP+($CURRENT−$TOP)/(@CELL("row",$TOP))−@CELL("row",B12..B12))*(@CELL("row",$TOP)) | | 111.111111111 |
| +$TOP+($CURRENT−$TOP)/(@CELL("row",$TOP))−@CELL("row",B13..B13))*(@CELL("row",$TOP)) | | 122.222222222 |
| +$TOP+($CURRENT−$TOP)/(@CELL("row",$TOP))−@CELL("row",B14..B14))*(@CELL("row",$TOP)) | | 133.333333333 |
| +$TOP+($CURRENT−$TOP)/(@CELL("row",$TOP))−@CELL("row",B15..B15))*(@CELL("row",$TOP)) | | 144.444444444 |
| +$TOP+($CURRENT−$TOP)/(@CELL("row",$TOP))−@CELL("row",B16..B16))*(@CELL("row",$TOP)) | | 155.555555556 |
| +$TOP+($CURRENT−$TOP)/(@CELL("row",$TOP))−@CELL("row",B17..B17))*(@CELL("row",$TOP)) | | 166.666666667 |
| +$TOP+($CURRENT−$TOP)/(@CELL("row",$TOP))−@CELL("row",B18..B18))*(@CELL("row",$TOP)) | | 177.777777778 |
| +$TOP+($CURRENT−$TOP)/(@CELL("row",$TOP))−@CELL("row",B19..B19))*(@CELL("row",$TOP)) | | 188.888888889 |
| | 200 | 200 |

FIG. 14A

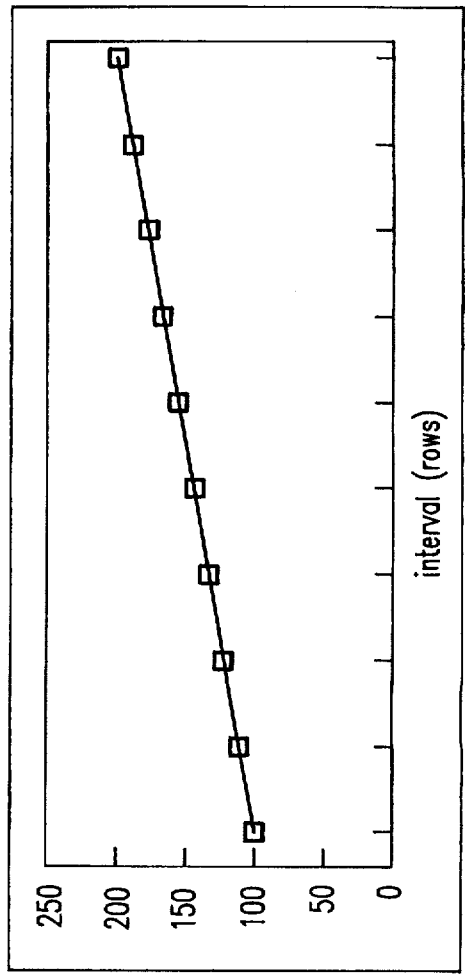

FIG. 14B

COMPUTED MEDICAL FILE AND CHART SYSTEM

BACKGROUND OF THE INVENTION

This invention relates to a computer software system of spread sheets and charts specialized for medical use, and more particularly, a data processing system which integrates and displays various kinds of medical data collected at irregular intervals from different sources such as doctors, nurses, laboratory personnel, and others.

Tremendous amounts of data are generated in daily medical practice. Based on this data, doctors make decisions about how to treat and care for a patient. Therefore, it would be better if the data could be integrated and more effectively presented to the doctors and other medical staff.

Computer systems are suitable vehicles for this purpose, but they have achieved only limited success in medical fields until now. One of the major reasons for this limitation is the irregular times when most medical data is collected. In the acute phase of a disease, or just after changing the therapeutic regimen, frequent tests are necessary, while in the chronic phase or in a stable condition, less frequent tests are sufficient.

In medical practice, there are various kinds of data coming from different sources. Some of them, for example, blood pressure, pulse rate, body temperature and urine volume, are observed by nurses several times everyday. Others like biochemical or serological tests are measured by a laboratory once a week, month, or even year.

Human factors exacerbate this irregularity. Sometimes a patient does not visit his or her doctor on the appointment date, and consequently, the necessary tests are not taken. There are considerable differences among doctors in the style of clinical testing and treatment of patients' problems. Clinical data may be easily missed by human error or a complicated hospital system.

In the prior art, computer systems which were developed for integration of medical information have not acquired the flexibility to fulfill the essential needs of a daily medical practice. Apart from computer systems, there have been only a few attempts to create more efficient medical information systems than the traditional handwritten medical charts or nurses' records. For example, Dr. Weed of Case Western Reserve University proposed a Problem Oriented Medical Record (POMR) system in 1969. *Medical Records, Medical Education, and Patient Care*, Lawrence L. Weed, Press of Case Western Reserve University, 1969. This system is aimed at a more comprehensive method of patient care by integrating different professionals' information. According to Dr. Weed's proposal, a POMR includes a flowsheet as well as problem list, patient's database, and follow up notes. A problem list is a list of each patient's problem related to the patient's illness. A flowsheet is a list of parameters that medical personnel monitor over an extended time period for patients (e.g., blood sugar level, urine volume, etc.). A flowsheet of each problem list shows changes of selected clinical and therapeutic data with time for each patient's problem.

In business, technology, and everyday life, charts have a universal appeal. People prefer to look at a pictorial representation of numbers rather than the numbers themselves. Medicine is no exception. For example, in a case presentation at a medical conference, a doctor often uses sophisticated charts to show a patient's clinical course. Though the charts may have a strong impact on an audience, it requires a long and painstaking effort to create these charts. Consequently, such charts are seldom used in daily clinical practice.

SUMMARY OF THE INVENTION

The present invention is titled "Computed Medical File and Chart System" and is referenced by the abbreviation "CMFCS". The CMFCS employs data processing techniques to overcome the above described difficulties in daily medical practice. It consists of a modified flowsheet of a Problem Oriented Medical Record (POMR), a program referred to as a Perception-Data_entry-Interpolation-Calculation unit (the PDIC unit) and related programs, and computer displayed medical charts.

The modified flowsheet has a standardized time scale represented by rows of the flowsheet. Depending on the clinical problem, hourly, daily, weekly, monthly, or other time scales can be chosen. The columns of the modified flowsheet are selected to obtain the most comprehensive graphic charts relating to the patient's problem. They include mostly the vital signs, laboratory data, and methods of therapy. Each column consists of the cell which contains the prototype formula for interpolation, the cell which contains the column title, the cell which contains the subtitle and the cells reserved for data entry.

The PDIC unit is the main component of the present invention. It consists of several parts and subroutines. When the operator opens a patient's file of the CMFCS, the modified flow sheet of POMR is displayed on the computer's screen. When the file is opened the first time, the cell pointer is placed at the cell address where the row and the column are frozen as the titles. However, if data has been previously input into the file, the cell pointer is placed at the last cell in which data was entered before the file was saved. The operator then moves the cell pointer to the position of the current cell in the flow sheet where data is to be entered and presses [control]+[D] on the keyboard to start the program of the PDIC system. At this point, the naming subroutine names the current cell (CURRENT), the top cell (TOP) and the bottom cell (BOTTOM). The program mimics the key operation [end]+[down]. The cell to where the cell pointer jumps is named BOTTOM and the cell pointer returns to CURRENT. The program also mimics the key operation [end]+[up]. The cell to where the cell pointer jumps by the operation is named TOP and the cell pointer returns to CURRENT. According to the relation of the rows of these cells, the perception subroutine recognizes the position of the current cell in the column, and the subroutine decides how to interpolate between the currently entered data and the previously entered data, or how to erase the cells with the interpolated data.

No interpolation is necessary if there are no empty rows separating the new data and the previously entered data. Interpolation is required if new data is entered into the modified flow sheet of the POMR by the operator, there is a cell containing real data above the new data, and there are one or more empty cells between the new data and the real data. Likewise, interpolation is required if new data is entered, there is real data below the new data, and there are one or more empty cells between the new data and the real data. If no real data exists before or after the new data, the remainder of the cells in the column will have no values in them, and no interpolation is done for these cells.

In some instances, previously interpolated data has to be erased. This is necessary when the operator erases a piece of real data, and previously interpolated data is above or below the erased real data. If a piece of real data is erased (for example, because it is in error), interpolated data which was calculated using that erroneous real data either is not needed any more, or it should be recalculated.

In the interpolation subroutine, each cell between the current cell and the cell of the preceding real data (i.e., the top cell) or each cell between the current cell and the cell of the following real data (i.e., the bottom cell) is interpolated in a predefined manner. The system calculates the position of the current column and copies the prototype formula written in the cell of row 148 in the current column to each cell in the interpolation range. The addresses of the copied formula are automatically adjusted to each row by Lotus 1-2-3. In one embodiment, the formula includes repeatedly determining for each interpolated cell an average of the preceding neighboring cell and the following neighboring cell. In another embodiment, a gradient between two points may be calculated. If the neighboring cell averaging method is used, the recalculation subroutine recalculates the average several hundred times and gets a virtual linear line between cells with real or known data. These interpolation methods are mostly used for expressing the changes in clinical parameters, such as laboratory tests or vital signs. Line charts with or without a multiple Y-axis are suitable for this purpose. For the presentation of other clinical parameters like the dosage of drugs or daily dietary intake, the interpolation method of the second embodiment and bar charts would be more suitable. In the prototype formula for drug dosage or daily dietary intake, each interpolated cell is just the same as the one preceding neighboring cell since these dosages and intakes do not change from day to day until the doctor orders such a change. Depending on the nature of the data or method of presentation in the visual chart, interpolation is not always necessary. Before exiting the program, the user should save the modified flow sheet of the POMR for later use.

The displayed medical charts are designed so that therapeutic data as well as clinical data are simultaneously shown on the same chart with the same time scale so that people can easily grasp changes in the clinical data and the influence of therapies. In addition to quantitative data, qualitative data like message notes could be shown on these charts. As the technology of multimedia progresses, methods embodying and showing graphical data like X ray films or endoscopic pictures on these charts can be developed.

The CMFCS is more powerful in a client server system of a computer network. Data stored in the server database management system (DBMS) is automatically selected and reconstructed in the flowsheet by the PDIC unit modified to perform this function (the modified PDIC unit). In this situation, while the server DBMS manages data from multiple entry sources, the client CMFCS extracts data from external data bases stored in the server DBMS, and reconstructs the data in the modified flow sheet of POMR. One of the features of the CMFCS is that retrospective data as well as current data can be reconstructed by the same manner.

The worksheet of the modified flowsheet is automatically and serially linked to external databases in different locations according to a directory table. The patients' data in the different external databases is extracted according to the data items in an output area, which are the same as the column titles of the modified flowsheet, and are located several rows above it. The extracted data is then reconstructed in the flowsheet by the modified PDIC unit.

Consequently, the use of CMFCS in medical studies or drug trials is most beneficial. Most medical studies are the observations of changes of given subjects over time. In clinical studies, observations on predefined time would be a rigorous obligation or serious limitation. It is possible to collect and compare many patients' data of a given data item observed at irregular periods by using the CMFCS because it has a standardized time scale and data interpolated by an appropriate formula. When the spread sheet program has a multi-layer function, the worksheets could be adjusted to the starting date of each patient's specific treatment in order to show more clearly the specific effects of the treatment on certain patients' problems. The character of the CMFCS might have a tremendous impact on drug trials in the future.

Accordingly, an object of the invention is to flexibly combine various parameters consisting of irregularly or regularly collected data from many different sources and to reconstruct them as a flow sheet for each patient's problem. The flow sheets enable doctors and other medical personnel to monitor and grasp the patient's disease condition more accurately and more quickly.

A second object of the invention is to allow medical personnel to easily produce the most comprehensive graphic charts relating to the patient's problem from patient data.

Another object of the invention is to allow users to automatically create patient records and charts from a server database management system.

A further object of the invention is to allow medical personnel to more accurately estimate missing clinical data in a patient's medical record.

A further object of the invention is to enable the collection and comparison of many patients' data of a given clinical parameter observed at irregular periods in medical studies or drug trials. When the spread sheet program has a multi-layer function, the worksheets can be adjusted to the starting date of each patient's specific treatment to show more clearly the specific effects of the treatment on certain patient's problems.

BRIEF DESCRIPTION OF THE DRAWINGS

FIGS. 2a through 2d illustrate several examples of modified flowsheets of a Problem Oriented Medical Record (POMR) employed in the CMFCS. The modified flowsheets have standardized time scales of weekly, daily, three times a day, and hourly as depicted in FIGS. 2a through 2d respectively;

FIG. 3a is an example illustrating a part of a modified flowsheet for a diabetic patient for use in the CMFCS;

FIG. 3b illustrates the interpolation formulas as well as the real data of the flowsheet of FIG. 3a;

FIGS. 7d, 7e and 7f illustrate the method used to calculate and decide the current column position;

FIG. 12a is an example of a flowsheet showing the collected information on serum creatine phosphokinase (CPK) levels in different patients with polymyositis and dermatomyositis observed during a certain period in the hospital.

FIG. 14a illustrates the gradient formula in use, and the values resulting therefrom; and FIG. 14b is a graph of the interpolated values of FIG. 14a.

DESCRIPTION OF A SPECIFIC EMBODIMENT

Figure 1:
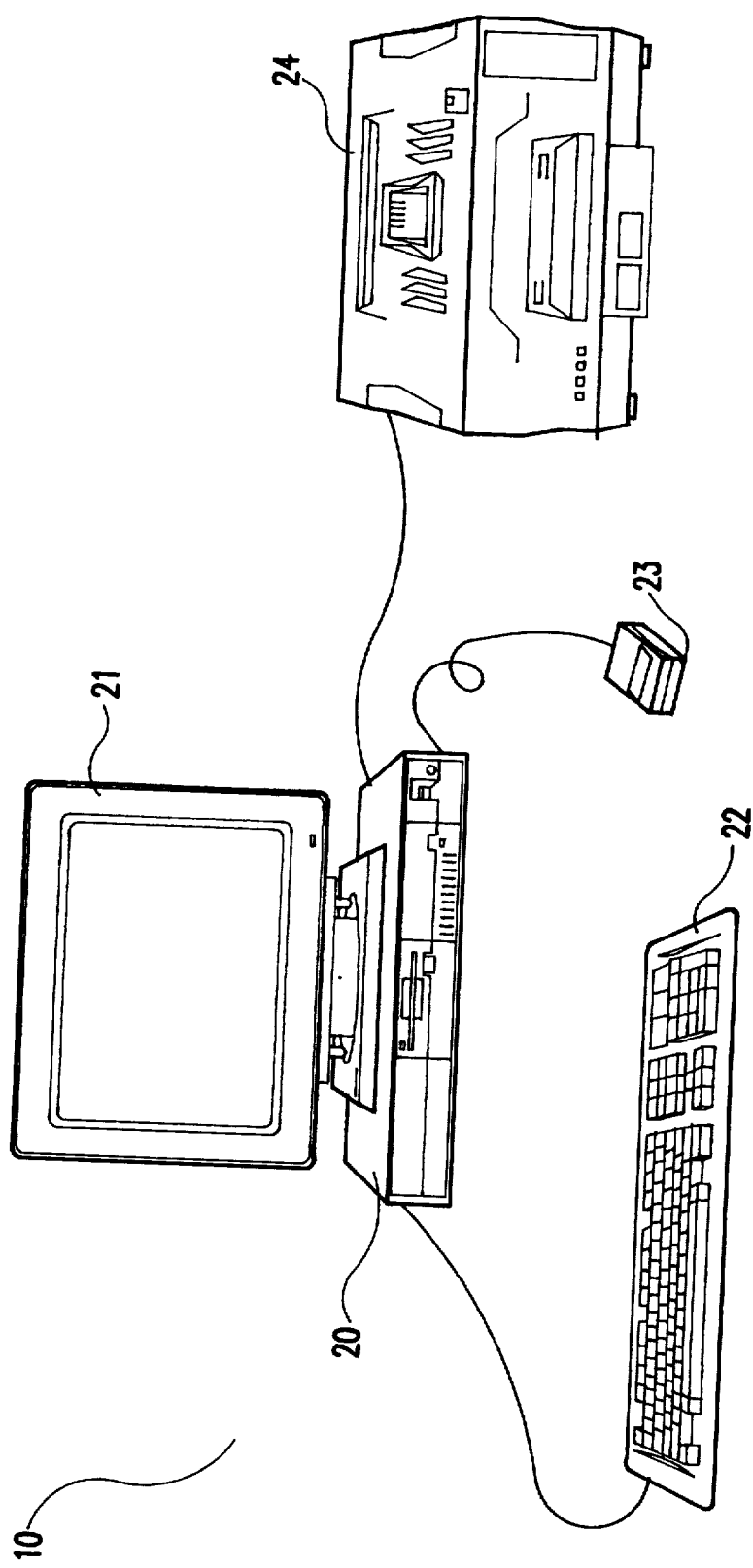
FIG. 1 illustrates a personal computer system which is used in the Computed Medical File and Chart System (CMFCS) and which is composed of a central processing unit (CPU), a display, a keyboard, a mouse and a color printer.

As shown in FIG. 1, the invention uses an ordinary personal computer system 10, which comprises a unit 20 within which is a central processing unit (CPU), a display unit 21, a keyboard 22, a mouse 23 and a color printer 24. The computer should be installed with a commercially available spread sheet program such as Lotus 123 for Windows (123/Win), Microsoft Excel, Borland Quattro Pro for Windows, or Infomix Wingz. Programs of graphical user interface (GUI) are much better than those of character user interface (CUI). Although the program of the present invention is written in the 'macro' language of Lotus 123 for DOS (123/DOS), it can also execute in Lotus 123/Win. Two versions of the source code are attached as an appendix.

In general, the invention uses the row and column data structure of the Lotus 123 spreadsheet or other comparable spreadsheet program to represent the rows and columns of a modified flowsheet of a Problem Oriented Medical Record (POMR). The rows of the flowsheet represent equally spaced time intervals (hours, days, weeks, months, etc.), and the columns represent a particular parameter that is monitored.

Figure 4:
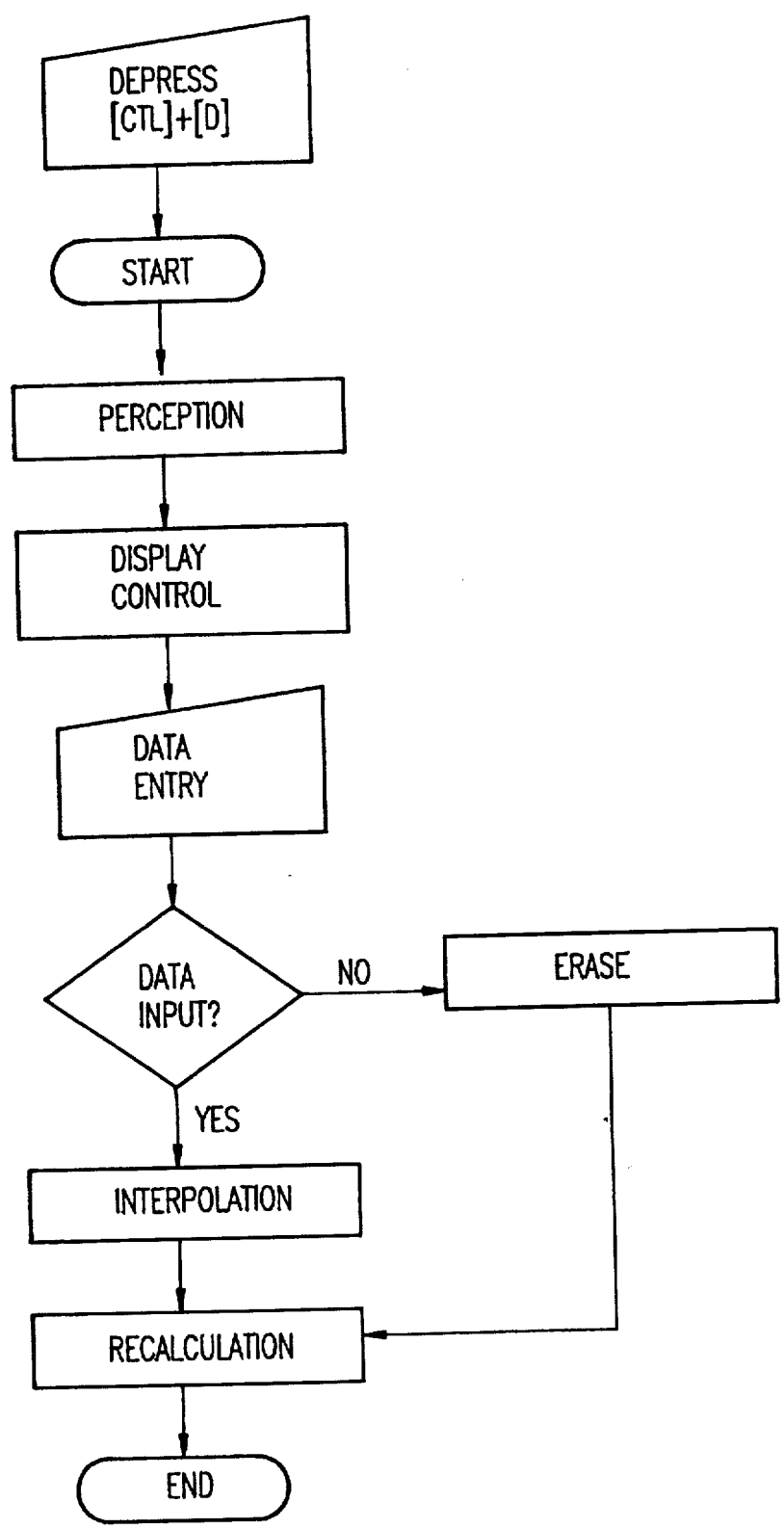
FIG. 4 is a flowchart of the software of the Perception-Data_entry-Interpolation-Calculation unit (the PDIC unit) used in the CMFCS.

A program written in the macro language of Lotus 123 carries out the interpolation and recalculation of the values for the flowsheet. This macro is referred to as the Perception-Data_entry-Interpolation-Calculation unit (PDIC unit). The PDIC unit accepts data from the user, places that data in a buffer and subsequently in the current cell, determines the range of cells to use in the interpolation, copies a prototype formula to the range, and interpolates and recalculates the data for those cells (see FIG. 4).

FIGS. 2a through 2d illustrate several flowsheets, each set up for the entry of data on a different time interval: FIG. 2a for a weekly basis, FIG. 2b for a daily basis, FIG. 2c for a three times per day basis, and FIG. 2d for an hourly basis. Any scale may be chosen for the rows of the flowsheet as long as each row represents the same time interval.

The flowsheet has a set of data items in each column representing clinical or therapeutic variables for a patient's problem. Doctors or other medical staff select data items to obtain the most pertinent information about the patient's problem. As shown in FIG. 3a, the columns include data observed by nurses or other staff, laboratory data, and methods of therapy. In particular, the patient's blood sugar (BS) level, the patient's glucosiliated hemoglobin level, the patient's urine volume (UV), the patient's intake of calories (Diet), and the amount of a drug taken by the patient (Daonil) are recorded for particular hospital days (HSP). The data shown in FIG. 3a represents actual observed data or administered treatments and is called "real data". Each column consists of the cell which contains the prototype formula for interpolation, the cell which contains the column title, the cell which contains the subtitle, and the cells reserved for data entry (FIG. 3b).

As to the cells themselves, before any data is entered, they are globally protected. No data can be entered directly into a globally protected cell. Before a user enters data into such a cell, the cell should be locally unprotected. There are two kinds of data—real or interpolated. Real data has non-hidden cell format, usually general or automatic, while interpolated data has hidden cell format which is not visible to the user. The PDIC unit determines the range of cells to use in the interpolation, and copies a prototype formula written in the row 148 of each column in the flow sheet to the interpolation range.

The stored formula is written in terms of the rows in relation to each other. When the program copies this formula to the rows of the flowsheet representation in the computer memory, which rows are to be interpolated, Lotus automatically adjusts this formula for the particular row in which it is placed. The system calculates the position of the current column and copies the prototype formula written in the cell of row 148 in the current column to each cell of the interpolation range. For example, in one embodiment of the invention, the interpolation formula averages the preceding cell and the following cell. Referring to FIG. 3b, this formula is stored in row 148 as (+C147+C149)/2. The notations C147 and C149 refer to rows 147 and 149 of column C, respectively. When this formula is copied to the rows to be interpolated, it is adjusted accordingly. For example, in FIG. 3b, the formula of row 148 (+C147+C149) /2, when copied down to row 158, is adjusted to take the average of the preceding row and next row, i.e., (+C157+C159)/2.

When the operators open a patient's file of CMFCS through ordinary Lotus 1-2-3's commands, a modified flow sheet of POMR is displayed on the screen. The titles of the columns and rows are frozen at the cell address C151, and when the file is opened for the first time, the cell pointer is placed at this cell address. If data has previously been input into the file, the cell pointer is placed at the last cell in which data was entered before the file was saved.

The operator moves the cell pointer to a position in the flow sheet where data is to be entered, or where data is to be erased, and presses [control]+[D] on keyboard 22 which starts the PDIC unit. At first, the program executes the subroutine COVER which indicates "execution" on the screen and freezes the screen. Then the program initializes the condition of the worksheets. The program enables global cell protection and sets recalculation iteration to one. The cell protection of a keyboard buffer cell named KBFR is locally unprotected. The cell format at the cell pointer is changed to general, the cell is named CURRENT, and the cell is locally unprotected. In Lotus 1-2-3, the range name is substituted for the address, and this allows Lotus 1-2-3 to act upon the range name rather than the cell addresses.

The program then mimics the key operation of pressing [end]+[down]. If there is a cell with data in the column between the current cell and row 8192 (the last row in Lotus 1-2-3), the cell pointer jumps to that cell, which is identified as bottom, and it is named BOTTOM. If there is no cell with data in the column between the current cell and row 8192, the cell pointer jumps to the cell of row 8192 of the column, which is identified as bottom, and it is named BOTTOM. The cell pointer returns to CURRENT.

In a similar manner, the program mimics the key operation of pressing [end]+[up]. If there is a cell with data in the column between the current cell and row 151 (the row where the column title is frozen), the cell pointer jumps to that cell, which is identified as top, and it is named TOP. If there is no cell with data in the column between the current cell and row 151, the cell pointer jumps to the cell of row 151 of the column, which is identified as top, and it is named TOP. Again the cell pointer returns to CURRENT.

According to the relation of the row of TOP and BOTTOM, the PERCEPTION subroutine then recognizes the position of the current cell in the data sequence of the column. This cell position determines what interpolation subroutine or erase subroutine will be executed following data entry as is described below.

After the PERCEPTION subroutine, the program enters the DSP_CTL (display control) subroutine which improves the visuality of the flow sheet, and the UNCOVER subroutine which unfreezes the screen. A data entry dialog box appears and indicates "Please input new data." If the operator inputs data, which is temporarily stored in the cell named KBFR (it means key board buffer), then the program executes the interpolation subroutines. If the operator inputs nothing, the program executes the erase subroutines. Again, the program executes the COVER subroutine which indicates "executing" on the panel and freezes the screen.

As explained above, if the user erases real data, interpolated data which was calculated using that real data may have to be erased or interpolated and recalculated again. The program has different erase subroutines and different interpolation subroutines, and the position of the data in the column recognized in the PERCEPTION subroutine determines which subroutine is executed.

Figure 6:
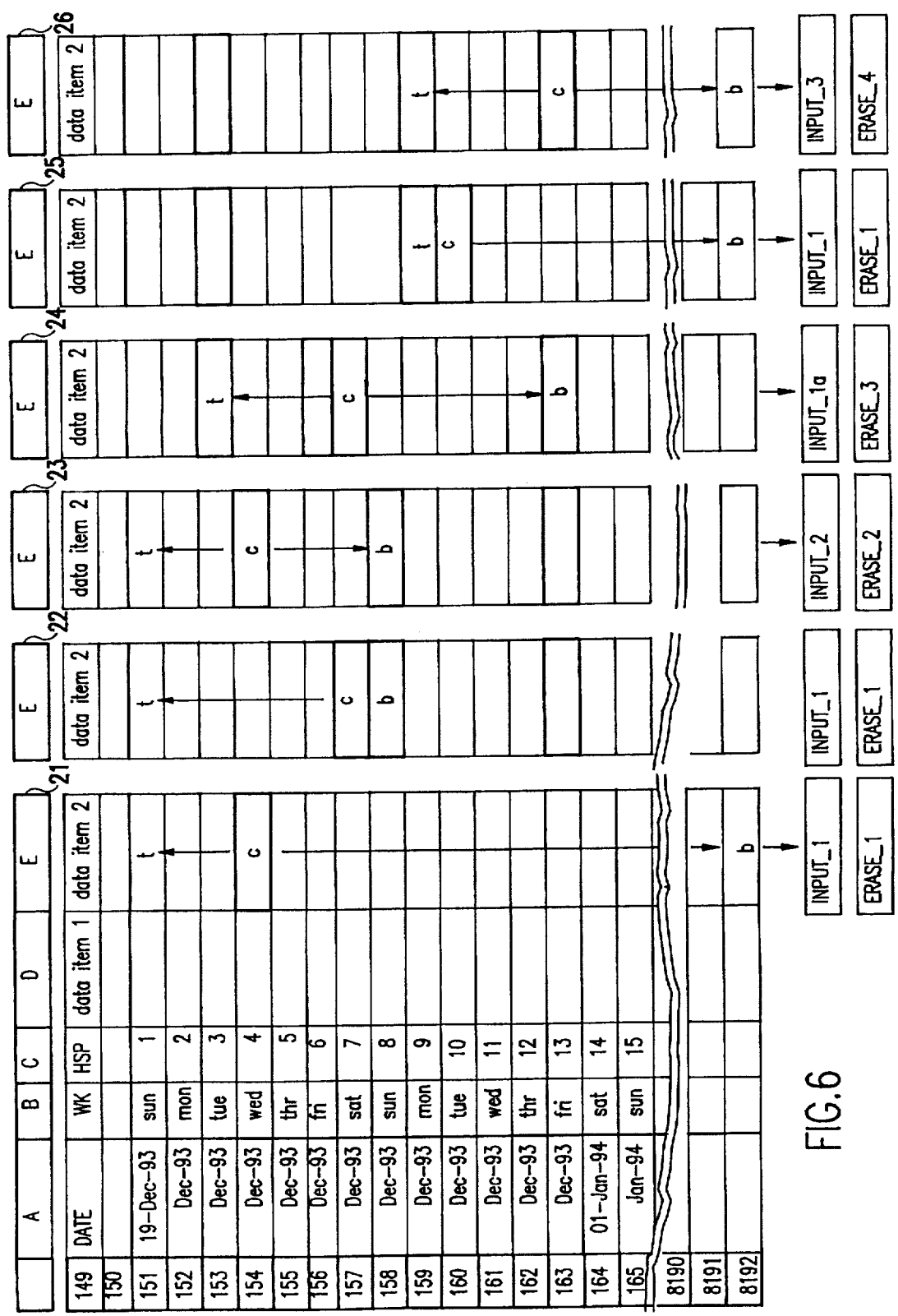
FIG. 6 schematically illustrates the decision logic used in the CMFCS so that a cell recognizes its relative position in the column. It also shows the interpolation and erase subroutines used in each case.
Figure 7A:
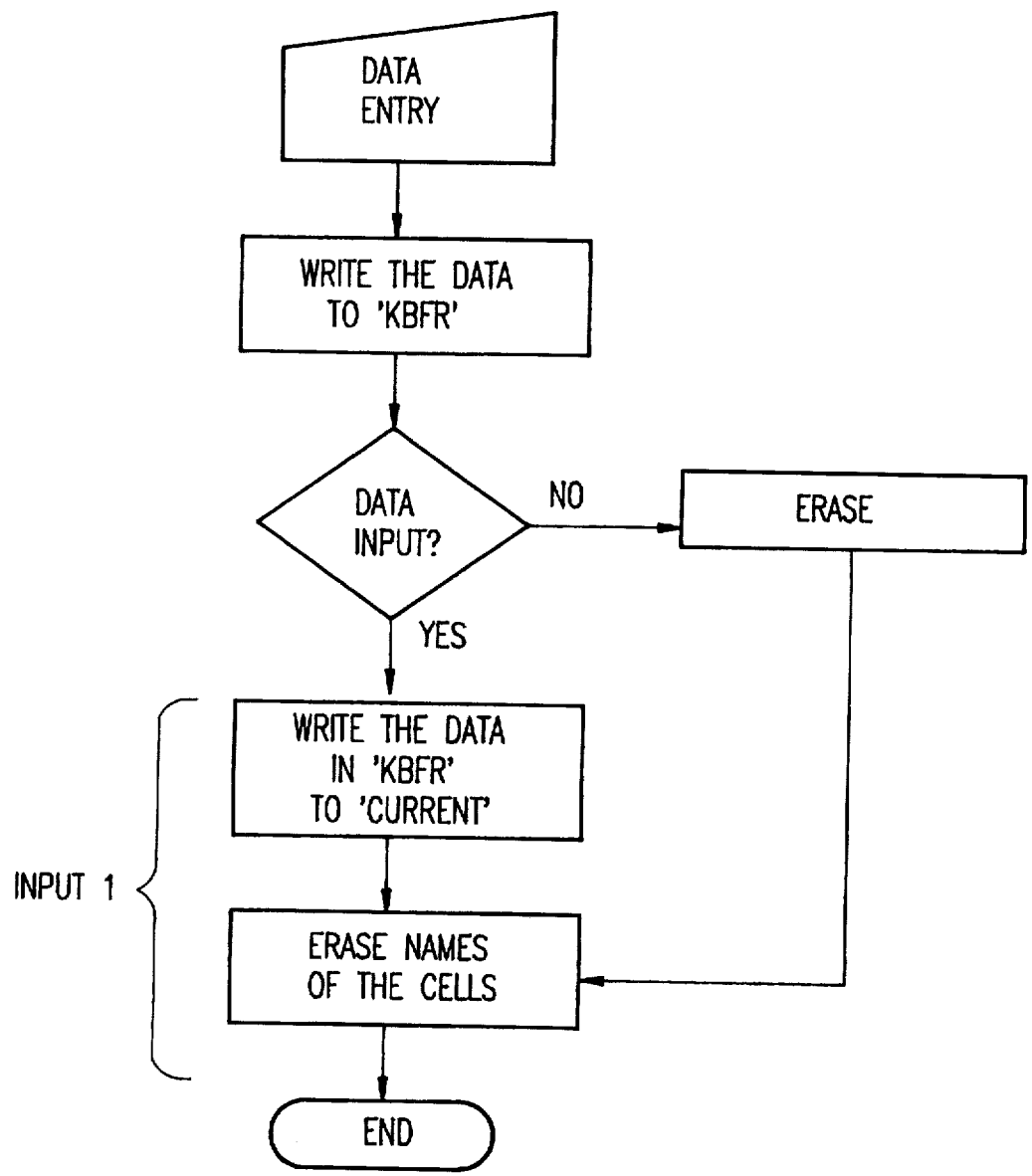
FIGS. 7a and 7b are more detailed flowcharts of routines INPUT_1 and INPUT_3 which include data entry, interpolation and recalculation routines used in the PDIC.
Figure 9A:
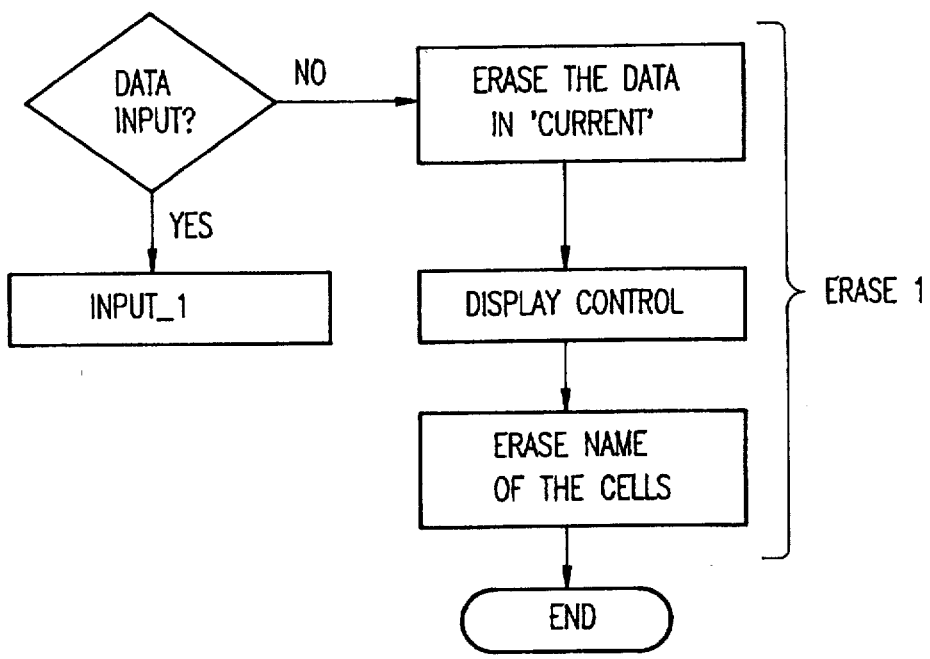
FIGS. 9a, 9b and 9c are flowcharts of the subroutines ERASE_1, ERASE_3 and ERASE_4 used in the PDIC.

Column 21 in FIG. 6 illustrates an example in which after the execution of the NAMING subroutine, the TOP pointer points to 151, the BOTTOM pointer points to 8192, and the cell pointed to by CURRENT is blank. In this example, the PERCEPTION subroutine will have recognized any data as the first data in the column, and if data were entered, it decides to execute INPUT_1. INPUT_1 is represented in the flow chart of FIG. 7a. The INPUT_1 subroutine writes the data that is temporarily stored in KBFR to the cell of the flowsheet to which CURRENT points. The cell is then protected and the CURRENT, BOTTOM and TOP pointer are deleted. Since this is the first piece of data to be entered into the modified flow sheet of the POMR, no interpolation occurs because there is no other data with which to perform an interpolation. If no data is entered (i.e., the user moves the cell pointer to the current cell and presses ENTER without entering any data), the program executes the ERASE_1 subroutine which unprotects the current cell, erases the data in the current cell, protects the current cell once again, and deletes the CURRENT, TOP and BOTTOM pointers as shown in FIG. 9a. Program execution then terminates.

In the example represented by column 23 of FIG. 6, the TOP pointer pointed to row 151, and the BOTTOM pointer pointed to a cell which is located above row 8192. In this example, the PERCEPTION subroutine will have recognized that the position of the CURRENT cell is above (i.e., having a lower cell number than) previously entered data. In this case, if data was entered, the program executes INPUT_2. The INPUT_2 subroutine first checks to see if the row of CURRENT is one above the row of BOTTOM. If it is, the program executes INPUT_1 as shown in column 22 of FIG. 6. Otherwise, INPUT_2 then defines an area of HOKAN extending from one row below CURRENT to one row above BOTTOM. HOKAN is a Japanese word meaning "interpolation". By calculating the position of the current column, the program copies the formula in row 148 of that column to the cells of HOKAN. As explained earlier, the addresses of the copied formula are adjusted to each row. The cell of CURRENT and the cells of HOKAN are then protected, and the names of CURRENT, TOP, BOTTOM and HOKAN are deleted. The program then executes the RECALCULATION or KEISAN subroutine. "KEISAN" means "calculation" in Japanese. In the example of column 23 of FIG. 6, HOKAN extends from row 155 to row 157. In the KEISAN (or RECALCULATION) routine, the program globally carries out the interpolation calculations for entire worksheets. If the user enters no data in the example of column 23 of FIG. 6, the program executes ERASE_2. ERASE_2 erases the data in the current cell and the cells below it until the cell pointer encounters a cell with real data and a non-hidden format. This erasure is necessary since the cells from CURRENT down to BOTTOM contain interpolated data which was interpolated using the data just erased in CURRENT. Because of the erasure of the data in CURRENT, the data in the cells below it are now no longer necessary. When the cell pointer encounters a cell with real data and non-hidden data format, program execution terminates.

Figure 9B:
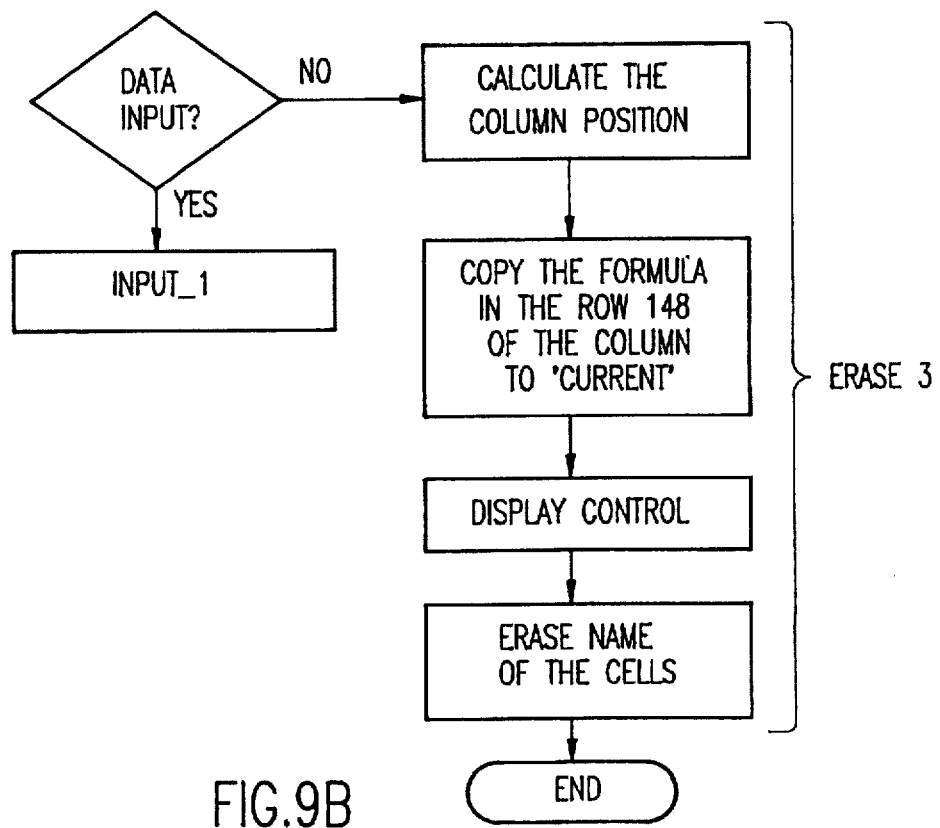

In the example of column 24 of FIG. 6, after the execution of the NAMING subroutine, the TOP pointer pointed to a cell which is greater than 151, and the BOTTOM pointer pointed to a cell which is less than 8192. In this situation, the PERCEPTION routine recognized that the CURRENT cell is between previously entered data. If data is entered, the program executes the INPUT_1a subroutine. Input_1a places the value which is in KBFR into the cell pointed to by CURRENT. INPUT_1a then invokes the KEISAN subroutine which globally recalculates interpolated cells in the entire flowsheet. After multiple recalculations, linear interpolations are obtained between the preceding real data and the CURRENT cell, and between the CURRENT cell and the following real data. In the example of column 24 of FIG. 6, the ERASE_3 subroutine is executed if no data is entered. In this routine, as shown in FIG. 9b, the cell is unprotected, the column position of the cell is calculated, and the formula of the row 148 in the column is copied to the cell. Then the subroutine KEISAN is executed to globally recalculate interpolated cells in the entire flowsheet. After multiple recalculation, linear interpolations are obtained between the preceding real data and the CURRENT cell, and between the CURRENT cell and the following real data. The current cell is then protected. The names TOP, BOTTOM and CURRENT are deleted. Program execution then terminates.

Figure 7B:
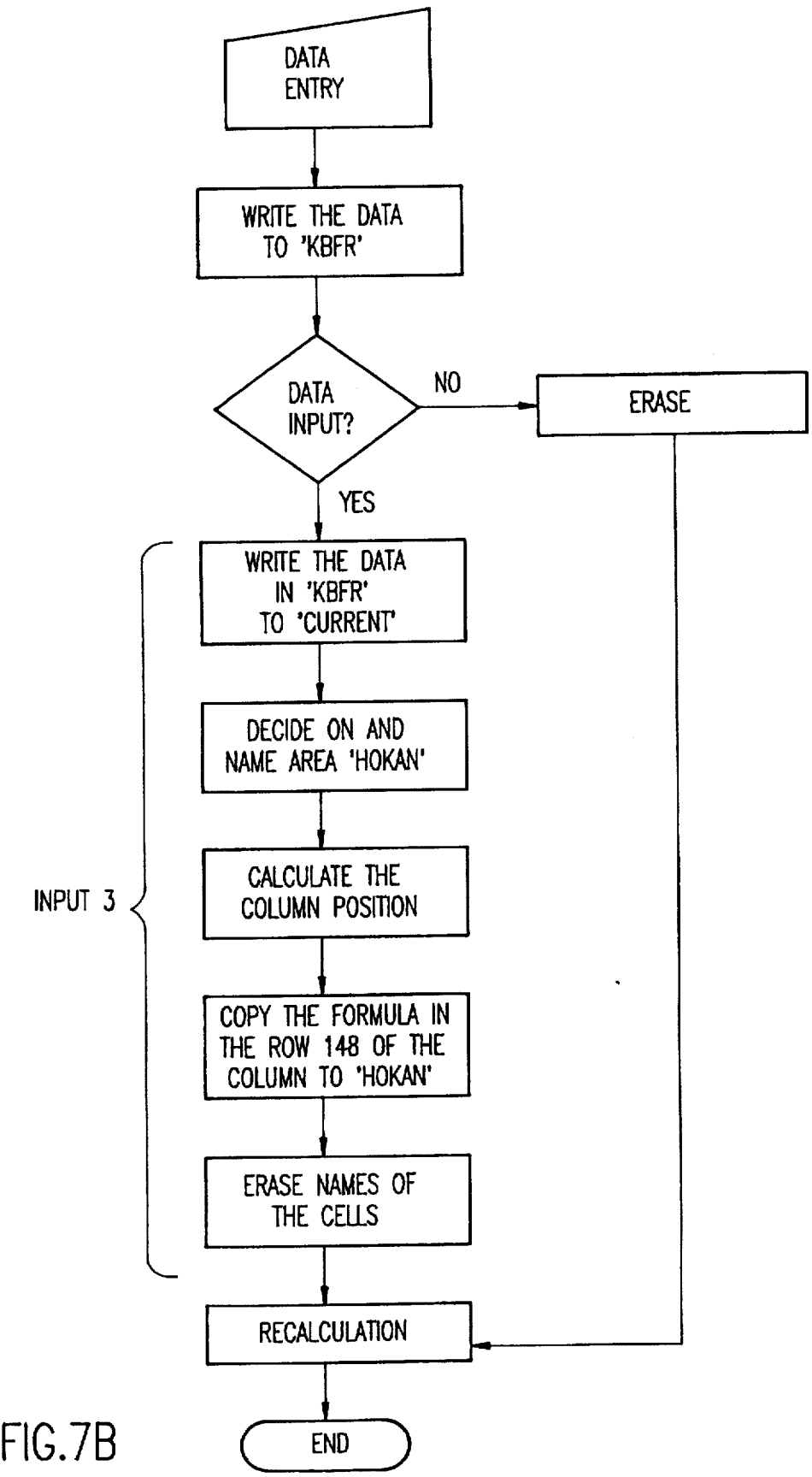
Figure 7C:
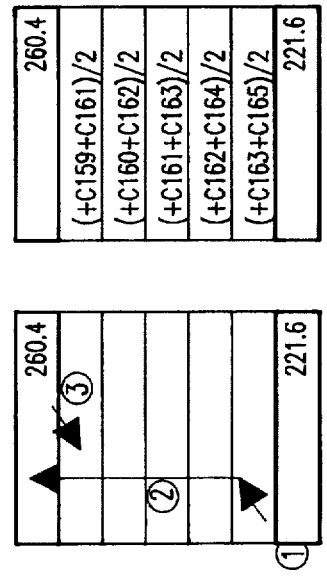
FIG. 7c shows a flowsheet illustrating in graphic fashion how the program defines the rows which it interpolates.
Figure 9C:
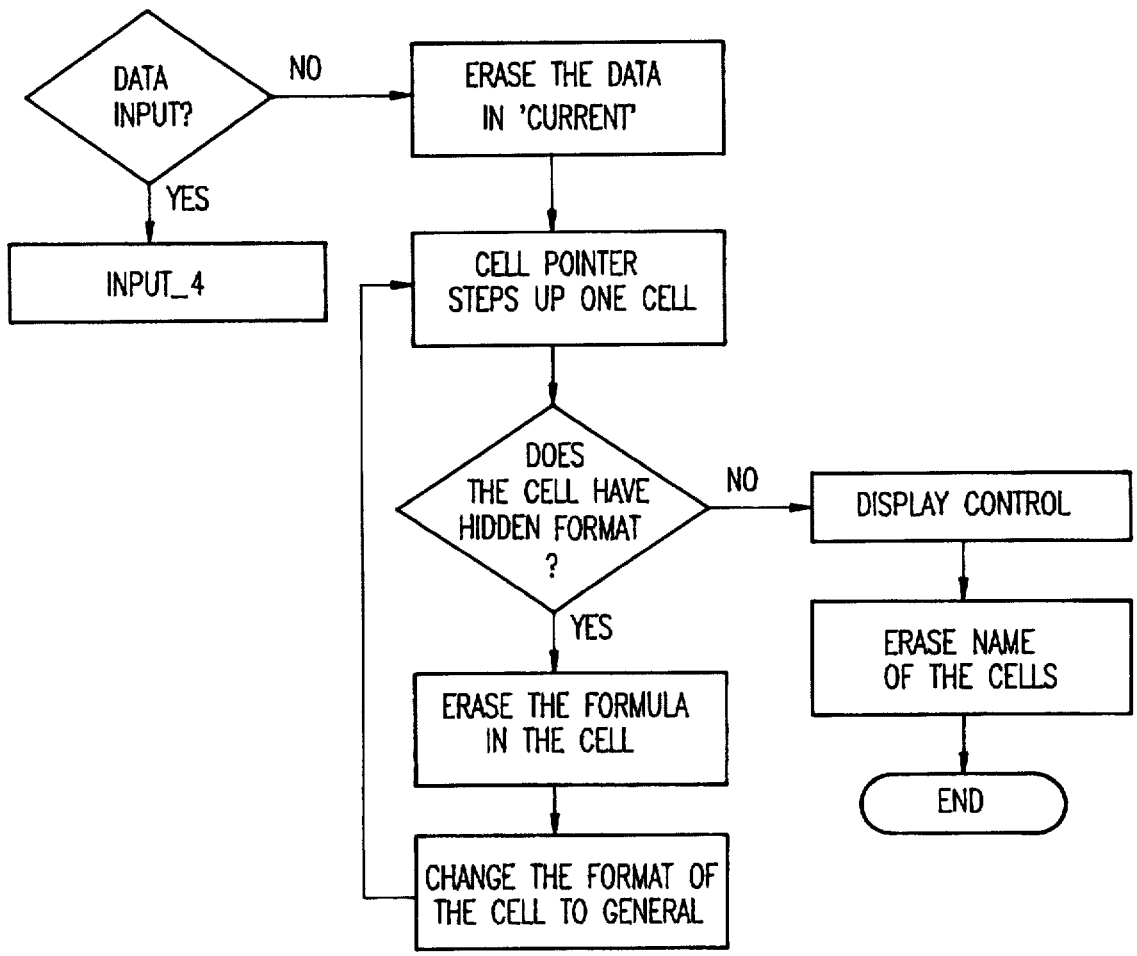

In the example of column 26 of FIG. 6, after the execution of the NAMING subroutine, the TOP pointer pointed to a cell which is greater than 151, and the BOTTOM pointer pointed to row 8192. The PERCEPTION subroutine will have recognized the entered data is more than one cell below the previous data. In this case the program executes the INPUT_3 subroutine if data is entered in the current cell. The INPUT_3 subroutine first checks to see if the row of CURRENT is one row below the row of TOP. If it is, the program executes INPUT_1 as shown in column 25 of FIG. 6. ERASE_4 (FIG. 9c) is executed if no data is entered in the current cell. If the entered data is more than two rows below the previous data, as shown in FIG. 7b, the INPUT_3 subroutine, after the data in KBFR is written to CURRENT, identifies the area between CURRENT and the cell with the last entered data as HOKAN. The INPUT_3 routine then executes the KEISAN subroutine to interpolate the data in HOKAN. FIG. 7c illustrates the cell pointer movement for INPUT_3. The cell pointer steps one cell above the CURRENT, which is the start point (the cell 164 in FIG. 7c). The cell pointer then jumps up to the last cell by mimicking the key operation of pressing [end]+[up], and steps down one cell, which is the end point (cell 160 in FIG. 7c). The cells of HOKAN are the cells 160 to 164, which are then unprotected. The program recognizes the cell address where the CURRENT cell is (FIG. 7d), obtains only the left 3 characters to extract the column label (FIG. 7e), and joins the column label with 148 to make the cell address where the prototype formula is written (FIG. 7f). Then the prototype formula in the cell is copied to the range HOKAN. As shown in FIG. 7c, and as explained earlier, the addresses of the copied formula are adjusted to each row. The cell of CURRENT and the cells of HOKAN are then protected, and the names of CURRENT, TOP, BOTTOM and HOKAN are deleted. Following the erasure of the cell names the program executes the subroutine KEISAN. In the KEISAN subroutine, the value in each cell in which the formula has been copied, (the HOKAN cells) is computed in accordance with the formula for each cell in sequence and this process is repeated a large number of times. By repeating the sequential calculation for the cells a large enough number of times, a linear interpolation of the values in each cell is obtained for the cells into which the formula was copied.

Figure 8A:
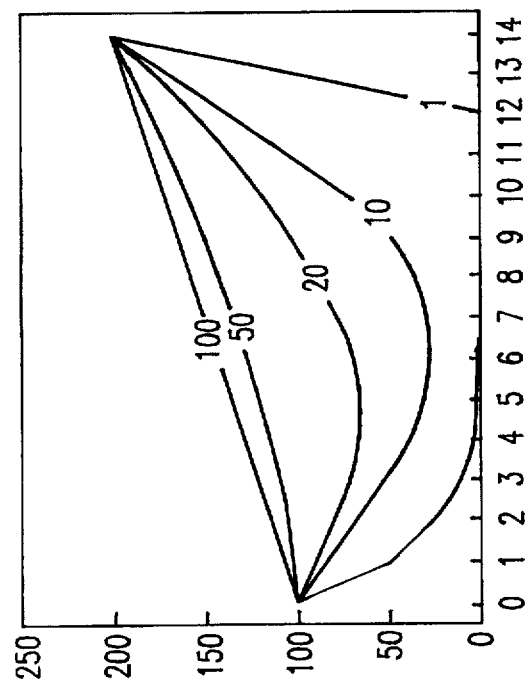
FIGS. 8a and 8b are graphs illustrating how repeated averaging recalculations obtain linear interpolation. When the interval between observed data is around 14 units, more than one hundred recalculations are needed (FIG. 8a). When it is around 30 units, more than four hundred recalculations are needed (FIG. 8b)
Figure 8B:
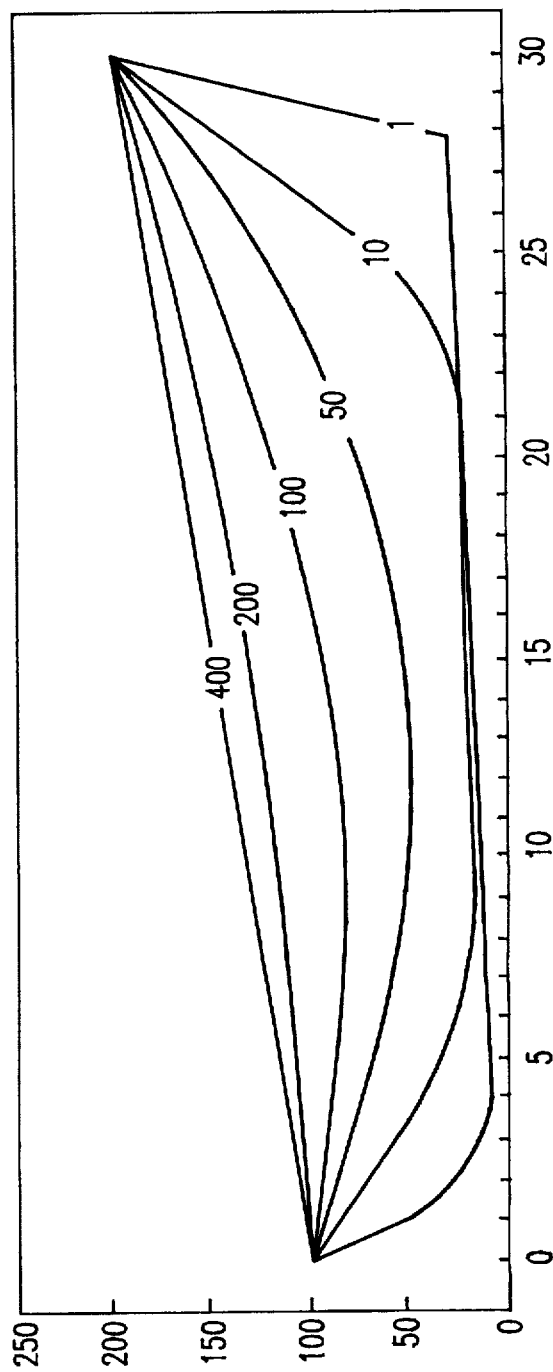

FIG. 8 shows how many recalculations would be needed to get a linear interpolation. When the interval between observed data is around 14 units, more than one hundred recalculations are needed (FIG. 8a). When the interval between observed data is around 30 units, more than four hundred recalculations are needed (FIG. 8b). After the recalculation of the HOKAN cells, program execution terminates.

The program executes the ERASE_4 subroutine if the user does not enter any data in the example of column 26 of FIG. 6. The ERASE_4 subroutine, illustrated in FIG. 9c, functions in a manner similar to that of ERASE_2. First, the cell pointer at CURRENT moves up one cell. If the cell has a hidden format, the formula of the cell is erased, and the format of the empty cell is changed to general. This process is repeated, until the cell pointer encounters a cell with real data and a non-hidden format. The cell pointer then jumps to CURRENT. The name of the cell and the data in the cell are erased, and program execution terminates.

Figure 13:
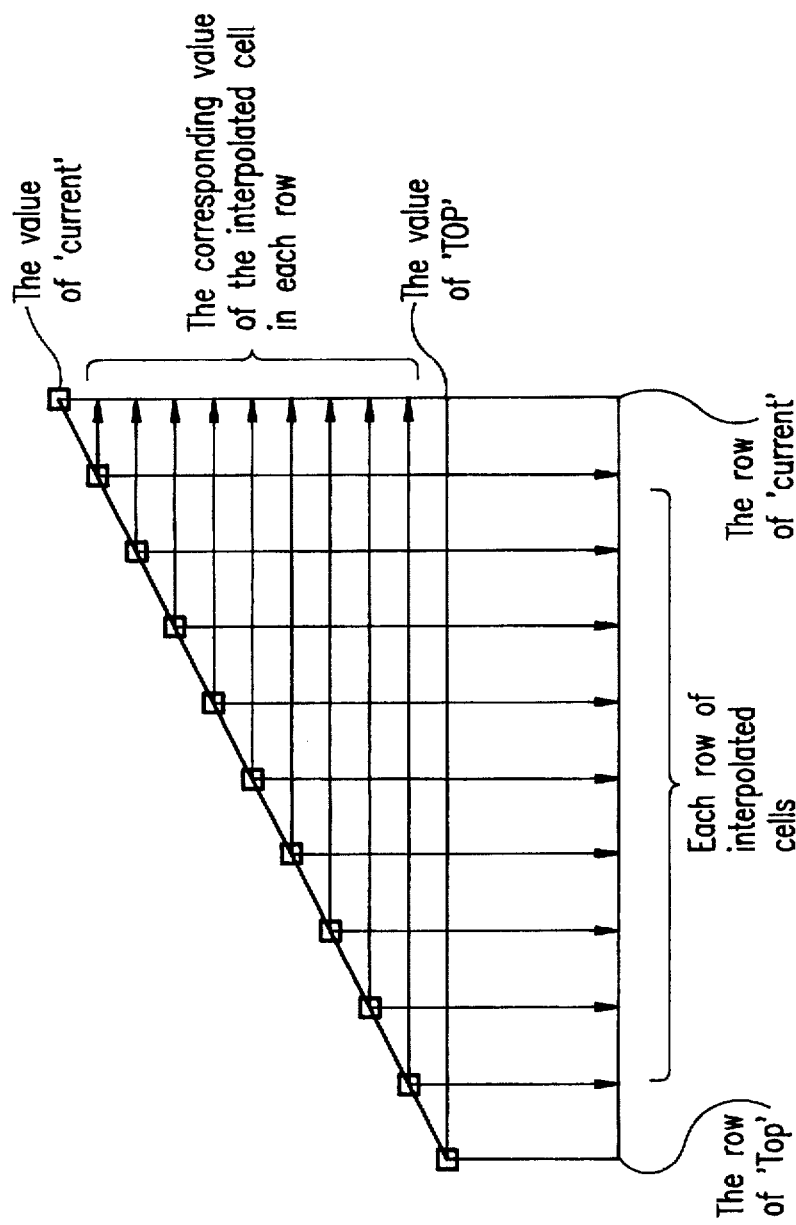
FIG. 13 graphically illustrates the gradient method of interpolation.

Instead of interpolating by repeated averaging as described above, the interpolation can use a built-in function of the Lotus program. This method is referred to as proportional allocation. In FIG. 13, the horizontal axis refers to the row numbers of the cells. The vertical axis represents the values of the cells. To interpolate between two items of real data, a gradient is multiplied by given variables and an intercept is added thereto. In FIG. 13, the intercept is the value of TOP, and the variable is the row number on the x axis. The gradient is arrived at by determining the difference between the value in the current and the value in the top cells, and dividing that difference by the number of rows between the current and the top cells. By substituting the row number for the variable, the corresponding value for each interpolated cell can be determined.

FIG. 14a illustrates an example of the proportional allocation method. The corresponding value of the interpolated cell of each row can be calculated directly by this method. The line chart obtained by this method is shown in FIG. 14b.

Figure 5:
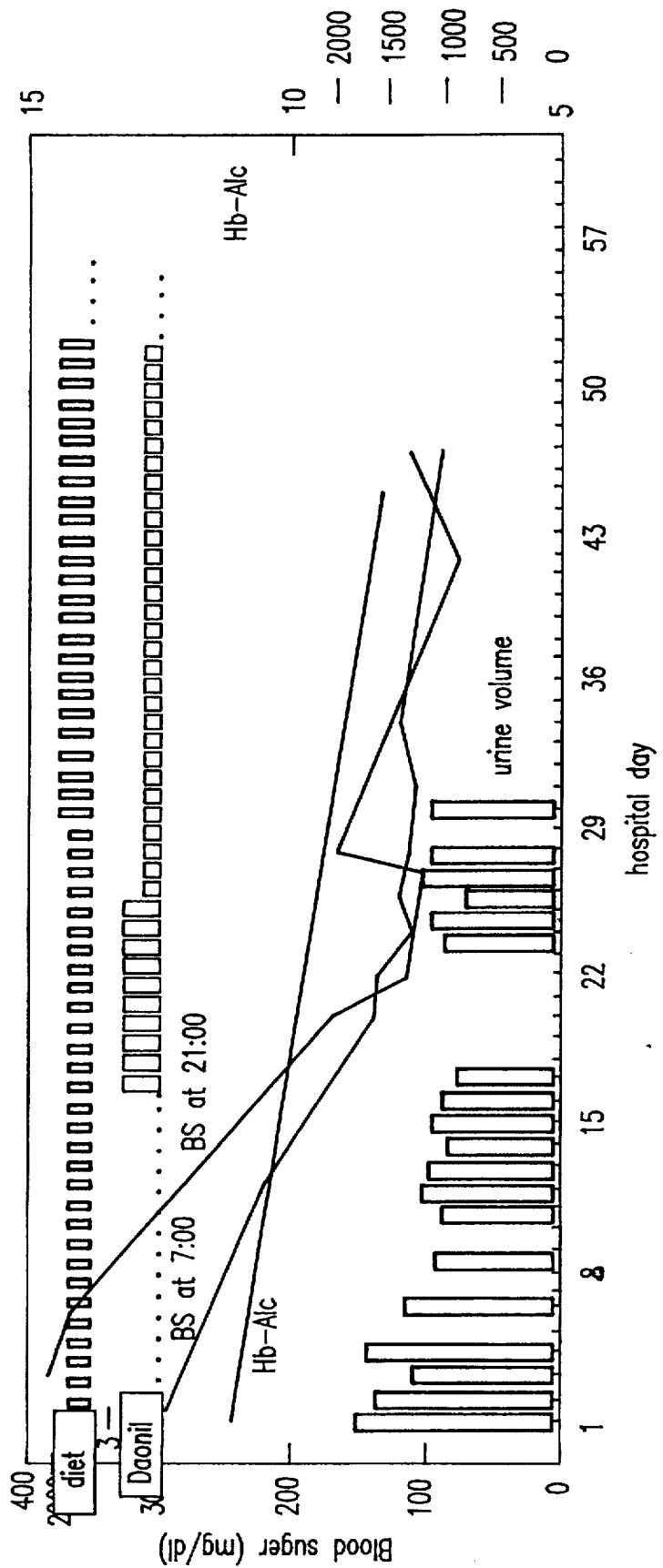
FIG. 5 illustrates a graphic medical chart using information shown in FIG. 3. The chart is designed so that therapeutic data as well as clinical data is simultaneously shown on the same chart with the same time scale.

It is contemplated that the graphical medical charts be designed so that therapeutic data as well as clinical data are simultaneously shown on the same chart with the same time scale so the user can comprehend changes in the clinical data and the influence of therapies. To create a graphical medical chart, several charts are created, which are then overlapped and combined using the same time scale. In the chart, the X-axis is always time (e.g., hourly, daily, weekly, monthly, or annually). Some charts have a double Y-axis. The line chart is suitable for expressing the changes in the clinical data. Other charts are bar charts, which are especially suitable for indicating therapeutic methods on the medical chart. For example, FIG. 5 shows when the therapy starts, the amount of drugs administered, and how much of a special diet is prescribed. Bar charts are also used for some laboratory or other observed data. The background of the overlapping charts is transparent, and the margins are clear. The title and/or the legends are erased or changed in their position or size. Based on the same time scale, other graphic remarks or short explanations with transparent backgrounds and free margins can be added to the chart if it is required. As the technology of multimedia progresses, graphical data like X ray films or endoscopic pictures could be embedded on the same time scale on the charts. Many predesigned templates for each clinical problem or diagnosis can be prepared. Doctors or other medical staff can select and modify the templates according to the specific needs in each patient case.

Figure 10:
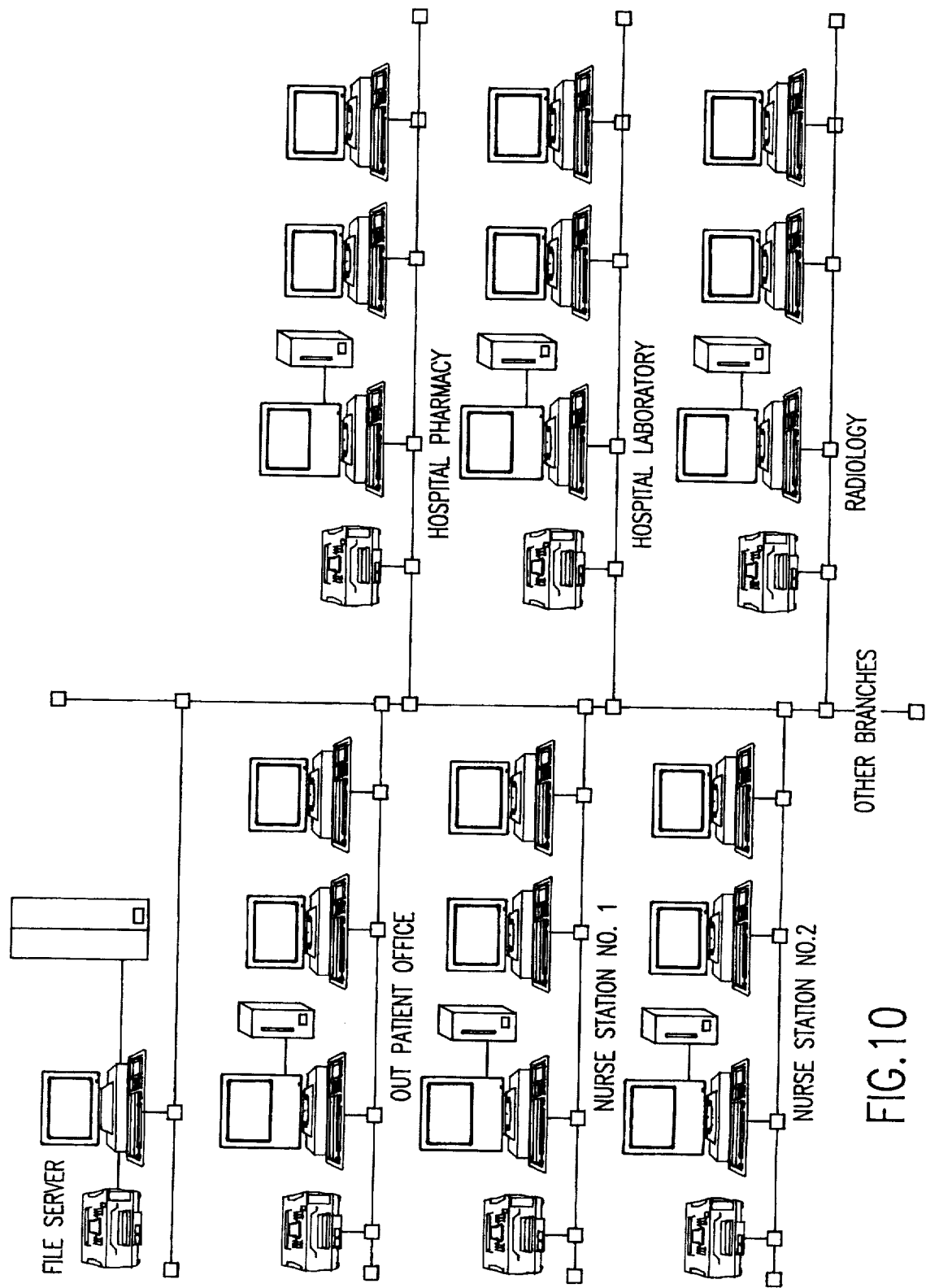
FIG. 10 illustrates a diagram of a client server system in which CMFCS is applied more effectively. In the illustrated system, data from different entry sources are managed by a server database management system (DBMS). Data stored in the server DBMS is automatically selected and reconstructed in the flowsheet by the modified PDIC unit.

By using a client server system as shown in FIG. 10, data stored in a server or other client database management system (DBMS) could be automatically selected and reconstructed in a flowsheet by the modified PDIC unit. In this situation, data from multiple entry sources is managed by the server DBMS. The CMFCS plays a role in data summation and presentation.

Figure 11:
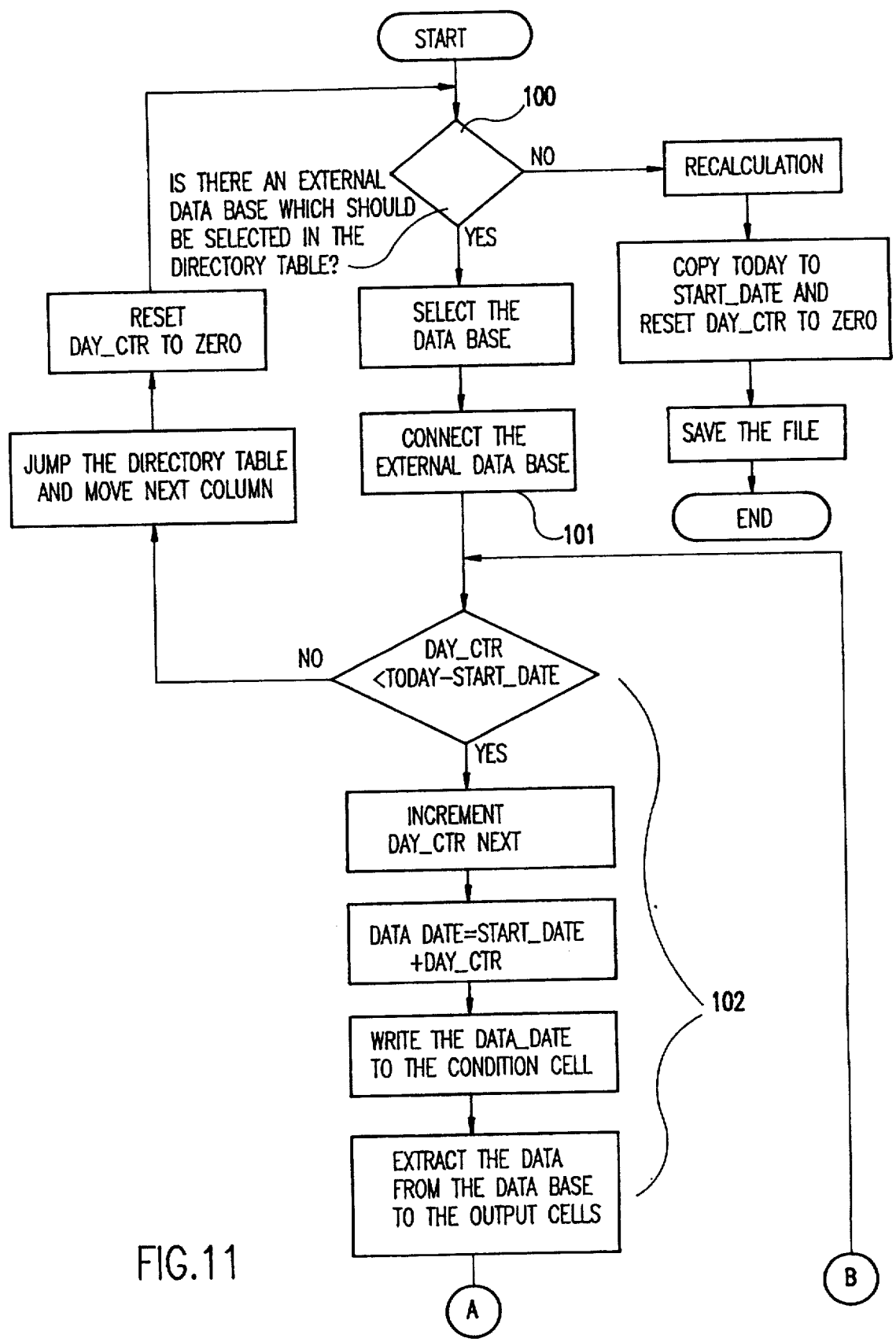
FIG. 11a is a flowchart of a program adjusted to a client server system. It can connect appropriate databases, extract new data, and integrate the data to the appropriate position on the modified flowsheet automatically.
FIGS. 11b and 11c show the directory table and date calculation table that are used in the program.
FIG. 11d illustrates how to carry and add data to the appropriate position on the flowsheet.
Figure 11A:
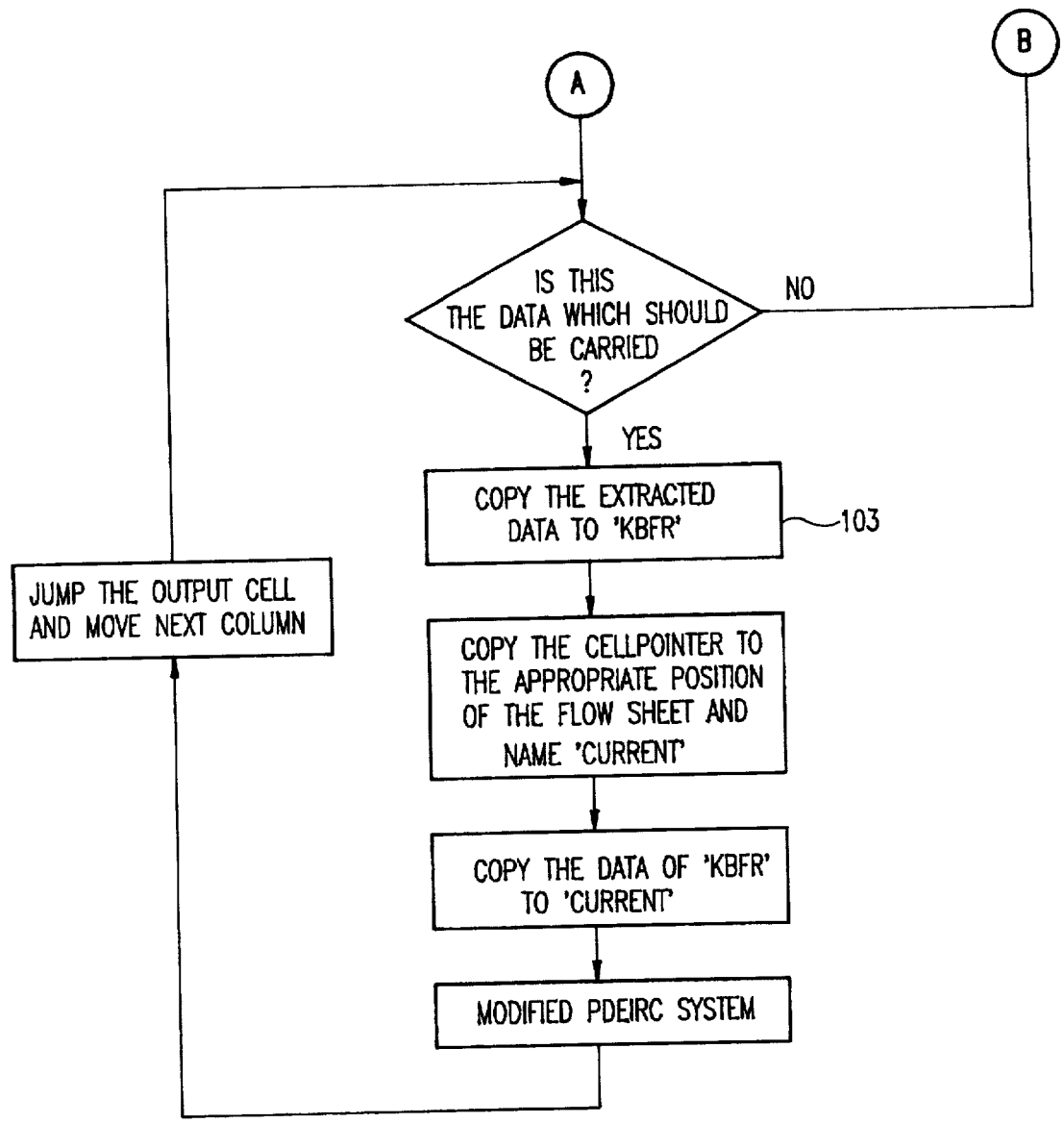

FIG. 11a is a flowchart illustrating the program of the CMFCS for a client server system in which the POMR worksheet of the CMFCS is linked to external databases stored in other locations. For this purpose, it is necessary for the CONNECTION unit to be able to determine the name of the directory, the file name of the external databases, the name of the condition area, and the output area in the worksheet. The CONNECTION unit does this via the directory table. FIG. 11b is an example of a directory table. In FIG. 11b, each column represents a separate external data base. The CONNECTION unit connects the worksheet to external databases in the sequential order of the columns in the directory table.

In this client and server system, the client personal computers as well as the server computers work in a nonstop operation. In the client personal computer in the nurse station, each patient's CMFCS file is automatically and serially opened, according with time schedule. The macro program automatically connects to external databases, extracts data consistent with criteria from the databases, and reconstructs the data in the modified flow sheet of the POMR. In Lotus 1-2-3, the macro program which has the special name \0 is automatically executed on opening the file.

After the start of the CONNECTION unit, the cell pointer jumps to the directory table, and determines whether there is an external database by checking the first entry in column 1 of the table, i.e., (DIRECTORY). If none exists, the path identified by "NO" at decision block 100 in FIG. 11a is executed. If one exists, the cells of the directory, that is, the file_name, the condition and the output in the column of No. 1 are assigned temporary names. The contents of the names (i.e., the FILE_NAME, CONDITION and OUTPUT of column 1) are copied to appropriate positions in the subroutine CONNECT of the program. The worksheet is linked to the external database by the execution of this subroutine. (Block 101 in FIG. 11a.)

Figure 11D:
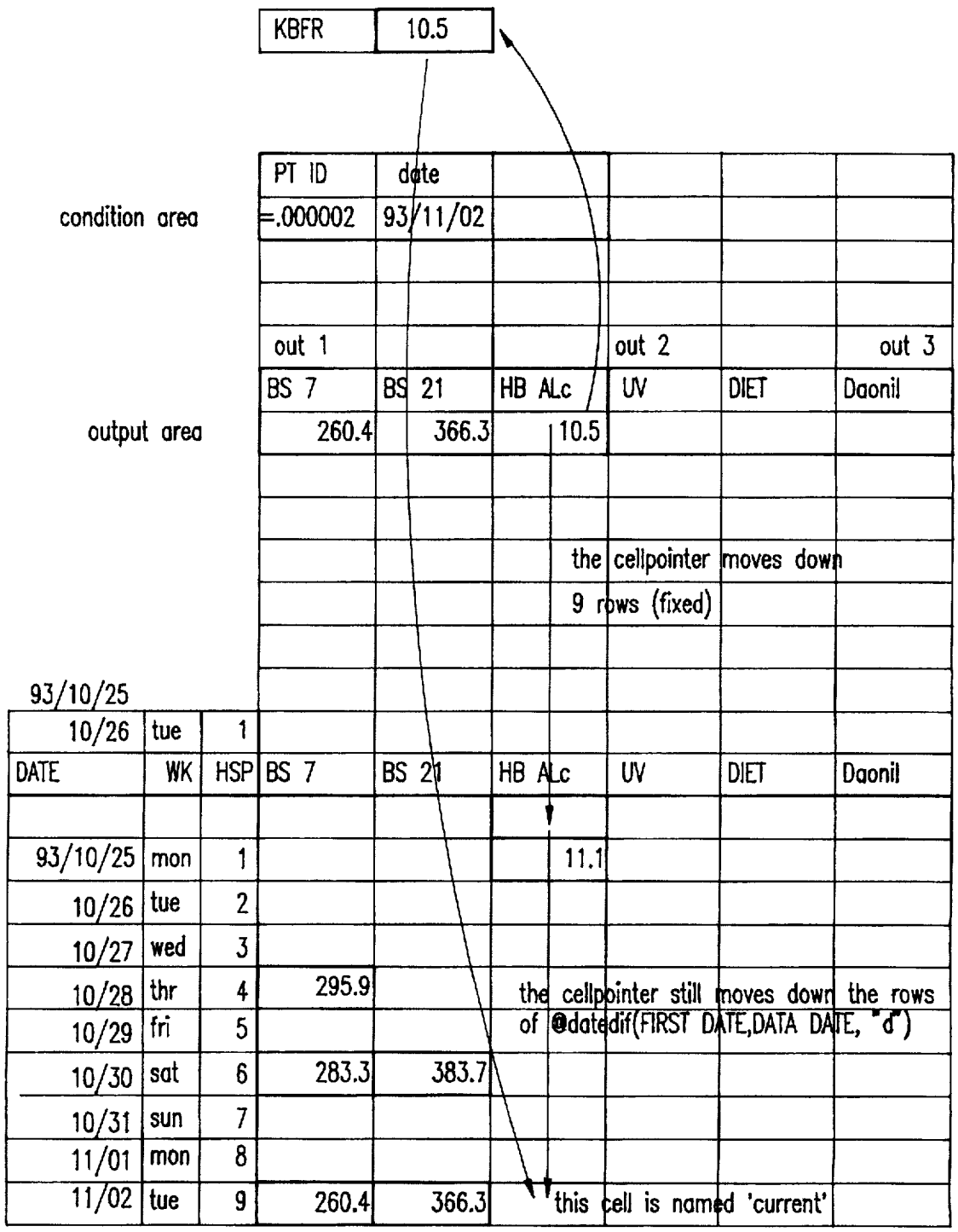

The program then enters the extraction loop (sequence 102). In this subroutine, the program refers to the date calculation table shown in FIG. 11c. The extraction loop is executed until the DAY_CTR (the day counter) is equal to the subtraction of START_DATE from TODAY. Next the DAY_CTR is incremented by 1, and the DATA_DATE is calculated by START_DATE+DAY_CTR. The DATA_DATE is then written to the proper cell in the condition area. The patient's data for the date contained in DATA_DATE is extracted from the external database according to the data items in the output area, which are the same as the column titles of the modified flowsheet, and are located 10 rows above it in parallel. The program writes this extracted data to the output area of a flowsheet. (See FIG. 11d.)

The program continues by executing the subroutine CARRY, in which the cell pointer jumps to the first output area and scans along the item titles until it encounters any extracted data, and the extracted data is copied to KBFR (block 103 in FIG. 11a). The cell pointer then moves down 9 rows which is the distance between the output area and the modified flowsheet, and then it moves down the number of rows equal to the difference between DATA_DATE and FIRST_DATE. The cell at the cell pointer is named CURRENT. (See FIG. 11d.) The program executes the modified PDIC unit (PDIC_2) which places the data in the proper location in the flowsheet.

There are only a few differences between the modified PDIC unit (i.e., the PDIC unit that reads an external database) and the ordinary PDIC unit. In the PERCEPTION subroutine, the first decision logic shown in FIG. 6 can be simpler, because the titles are not frozen in the situation. When the row of TOP is less than 151, and the row of BOTTOM is 8192, INPUT_4 is selected as the interpolation subroutine. The interpolation subroutines, INPUT_4, INPUT_5 and INPUT_6 do not have the codes for the data entry dialog box from the keyboard, but the data stored in KBFR is directly written to CURRENT. The following interpolation and recalculation subroutines are the same as those of the ordinary PDIC unit except for the end of the program. The modified PDIC unit does not have the erase subroutine and the display control subroutine.

In the modified PDIC unit, the cell pointer returns to the cell in the output area, moves to the next column, and the program continues. The cell pointer reaches the end of the titles in the output area, then the program returns to the extraction loop to extract data on the next day from the external database. When the DAY_CTR reaches a point equal to the subtraction of the START_DATE from TODAY, the cell pointer goes back to the directory table to link the worksheet to the next external database identified in the next column of the DIRECTORY row, and the DAY_CTR is reset to zero. When there is no external database which could be selected in the directory table, the date of TODAY is written as the START_DATE, and the DAY_CTR is reset to zero. The recalculation subroutine is executed, the worksheet is saved, and the program terminates.

The CMFCS applies to medical studies or drug trials. In order to illustrate the usefulness of the CMFCS for medical studies, an actual study is described in relation to FIG. 12.

FIG. 12a is a part of the collected information on serum creatine phosphokinase (CPK) levels in patients with polymyositis and dermatomyositis observed during a certain period of time in the hospital. The rows refer to hospital days, and the columns identify patients' names or patients' identification numbers. The data of a single patient's column is collected at irregular intervals. The data of combined columns in the cases of many patients are more random.

Figure 12B:
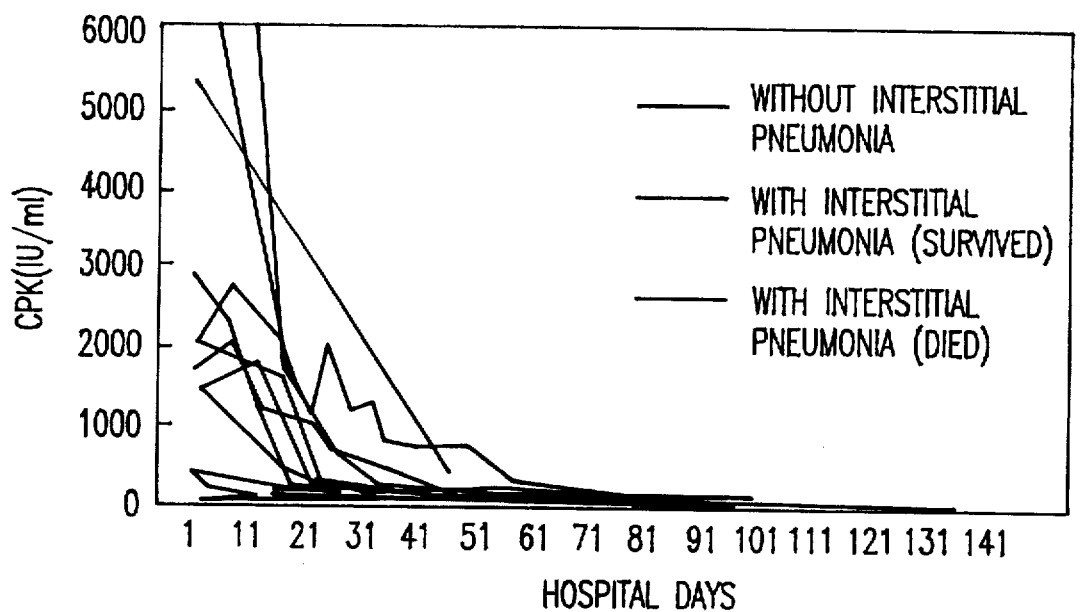
FIGS. 12b and 12c are respectively graphic line charts of CPK and lactate dehydrogase (LDH) in the myositis patients.
Figure 12C:
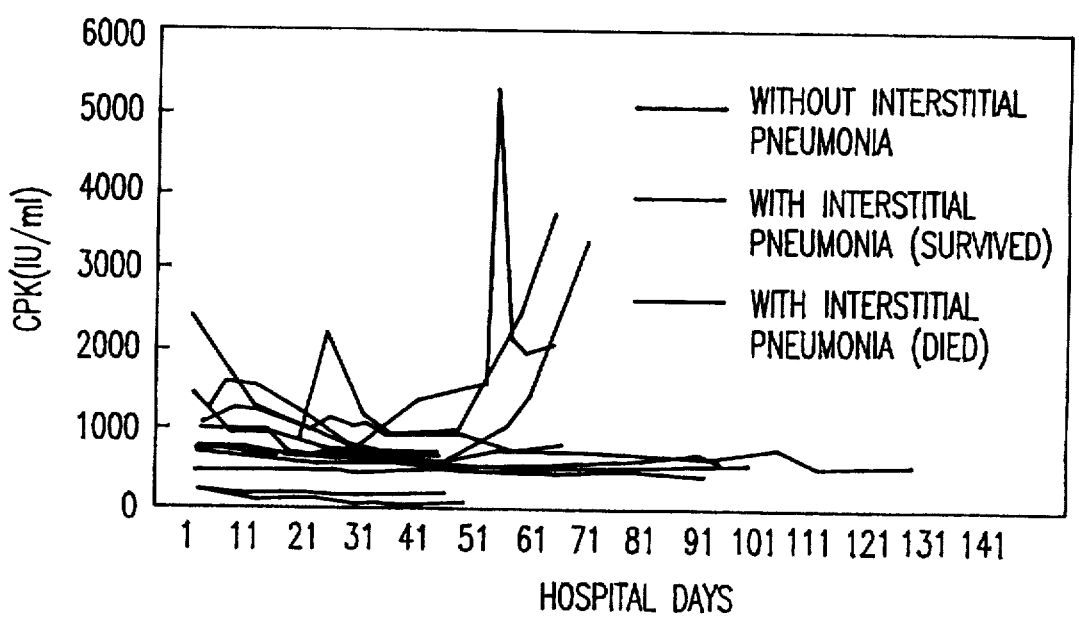

Based on these tables of the CMFCS, line charts of CPK and lactate dehydrogase (LDH) in the myositis patients are made as shown in FIGS. 12b and 12c respectively. It is possible to collect and compare many patients' data of CPK and LDH observed at irregular intervals by using the CMFCS, because it has a standardized time scale and virtual data is interpolated by an appropriate formula.

In this study, 15 patients with polymyositis or dermatomyositis were classified into three groups; 6 patients without interstitial pneumonia (IP) who survived, 5 patients with IP who survived, and 4 patients with IP who died. Serum CPK levels decreased after hospital admission in all three groups. This finding suggests that steroid therapy after admission was very effective for myositis in these patients. Three out of 4 patients with IP who died had very low levels of CPK at the time of hospital admission. In other words, the patients showed skin manifestations with minimal myositis.

Serum LDH levels also declined in most patients after admission. In 3 out of 4 patients with IP who did not survive, however, LDH levels rose in spite of intensive steroid or immunosuppressive treatment over the length of their hospital stay. Discrepancy between serum CPK and LDH levels suggested grave prognosis in the patients with myositis in this study.

Figure 12D:
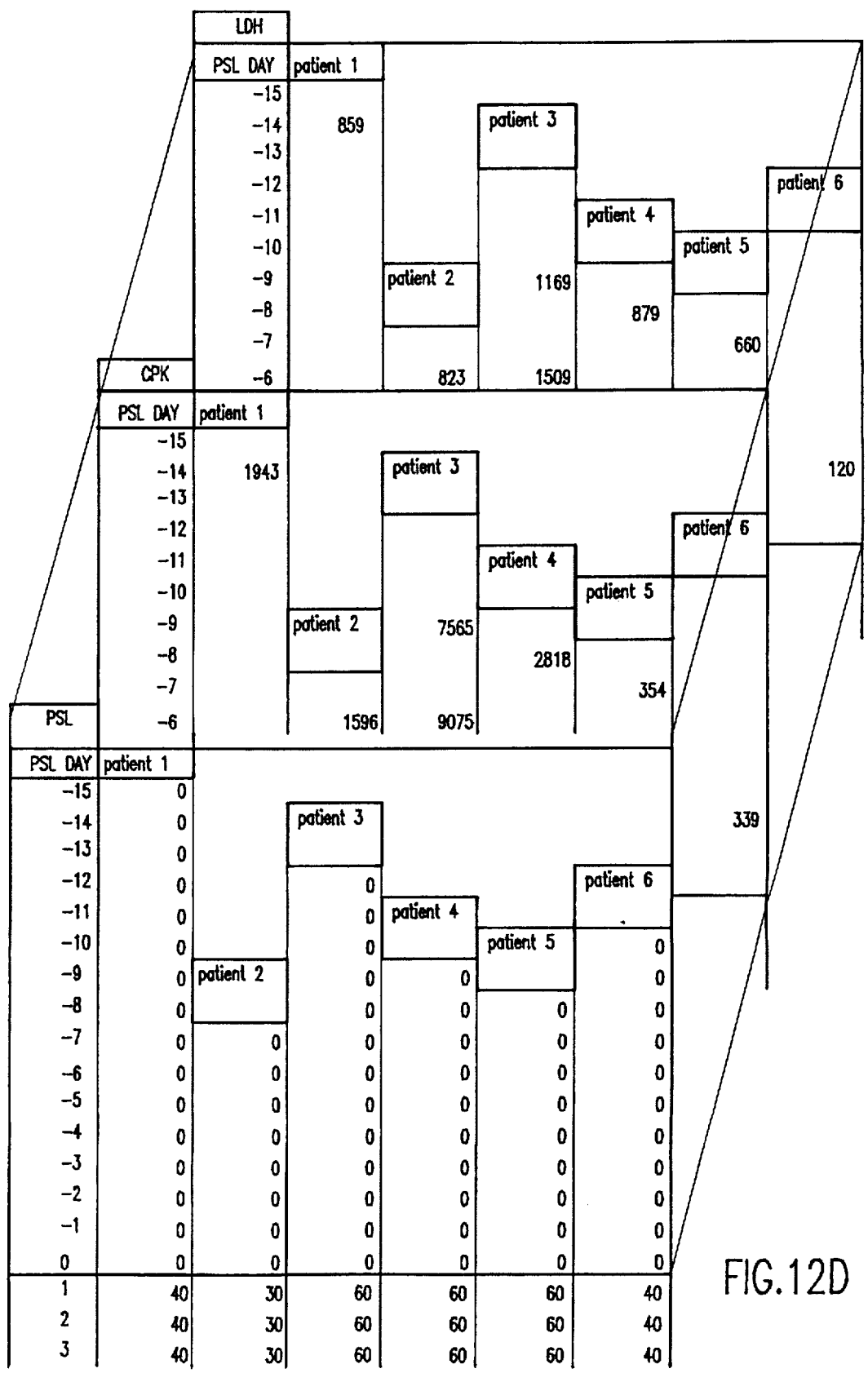
FIG. 12d is a conceptual drawing of multilayer worksheets adjusted to the starting date of each patient's steroid administration.

Newer spread sheet programs have a function of multi-layer worksheets. This makes it possible to perform more specific analysis of the clinical effects of therapeutic factors such as the administration of drugs. FIG. 12d is a conceptual drawing of a multi-layer worksheet adjusted to the starting date of each patient's steroid treatment. This method can show more clearly the specific effects of steroid therapy on myositis patients.

While this invention is particularly useful and adapted for daily medical practice, general medical studies, and especially drug trials, the concept of the invention is applicable to studies of other natural phenomena or other situations. The above description of the invention is of a preferred embodiment of the invention and modification may be made thereto without departing from the spirit and scope of the invention, which is defined in the appended claims.

CMFCS (original for a C/S system)

The program list of the Computed Medical File and Chart System
(for Client Server System)
version 1.1 (original version)

Yasuo Kumagai,M.D.
January 4, 1995

*directory table*

|  | no_1 | no_2 | no_3 | no_4 |
|---|---|---|---|---|
| DIRECTRY | c:\CMF\CMFC | c:\CMF\CMFC | c:\CMF\CMFC | c:\CMF\CMFCS\NURSE |
| FILE_NAME | LABO_DAT | UV_DIET | DRUGS |  |
| CONDITION | COND_1 | COND_1 | COND_1 |  |
| OUTPUT | OUT_1 | OUT_2 | OUT_3 |  |

KBFR   1,25            SWITCH_1   ERASE_4

```
 1  DB_CHANGE (IC)  {menu}wgpd
 2                  {menu}wgnl~
 3                  {goto}DIR_TABLE~
 4  DBCHANGE_1      {}
 5                  {if @cellpointer("type")="b"}{RESET_1}{quit}
 6                  {menu}mcDIR_TEMP~~{d}
 7                  {menu}mcFN_TEMP~~{d}
 8                  {menu}mcCOND_TEMP~~{d}
 9                  {menu}mcOUT_TEMP~
10                  {let DIRECTRY,DIR_TEMP}
11                  {let FILE_1,FN_TEMP}
12                  {let FILE_2,FN_TEMP}
13                  {let CONDITION,COND_TEMP}
14                  {let OUTPUT,OUT_TEMP}
```

*date calculation table*

| DAY_CTR |  | 0 |
|---|---|---|
| FIRST_DATE |  | 01/01/94 |
| START_DATE |  | 04/01/94 |
| DATA_DATE |  | 04/01/94 |
| TODAY |  | 30/01/94 |
| DATE_DIF |  | 3 |

| COLCAL_1 | $A$1 |
| COLCAL_2 | $A$ |

Kumagai, MD — CMFCS (original for a C/S system)  -2-

```
15  {menu}rndFN_TEMP~
16  {menu}rndCOND_TEMP~
17  {menu}rndOUT_TEMP~
18  {CONNECT}

19 RESET_1  {let DAY_CTR,0}
20          {let START_DATE,TODAY}
21          {KEISAN_2}
22          {menu}wgpc
23          {menu}fs~b~
24          {return}

25 KEISAN_2 {menu}wgri50~
26          {calc}
27          {calc}
28          {calc}
29          {calc}
30          {calc}
31          {calc}
32          {calc}
33          {calc}
34          {menu}wgri1~
35          {return}

36 CONNECT   {onerror CONNECT_1}
37           {menu}1dav~{esc}
38           c:\CMFCS\NURSE
39           ~{esc}
40           DRUGS
41           ~q
42 CONNECT_1 {menu}dqi
43           DRUGS
```

Kumagai, MD  CMFCS (original for a C/S system)  - 3 -

44  ~
45  COND_1
46  ~?
47  OUT_3
48  ~
49  {LOOP}
50  {return}

51 LOOP  {if DAY_CTR>TODAY-START_DATE}{RESET_2}{DBCHANGE_1}
52  {EXTRACT}

53 RESET_2  {goto}DIR_TEMP~
54  {menu}rndDIR_TEMP~
55  {let DAY_CTR,0}
56  {return}

57 EXTRACT  {let DAY_CTR,DAY_CTR+1}
58  {menu}rvDATA_DATE~COND_DATE~
59  {menu}dqe~q
60  {CARRY}

61 CARRY  {goto}OUT_1~
62 CARRY_1  {if @cellpointer("type")="b"}{LOOP}
63  {d}
64  {if @cellpointer("type")="b"}{u}{r}{CARRY_1}
65  {if @cellpointer("contents")=0}{u}{r}{CARRY_1}
66  {menu}rncEXT_CELL~~
67  {menu}cEXT_CELL~KBFR~
68  {d 9+DATE_DIF}
69  {PDIC_2}

CMFCS (original for a C/S system)

```
70 PDIC_2              {menu}rfg~
71                     {menu}nuKBFR~
72                     {NAMING}
73                     {PERCEPTION_2}
74                     {CARRY_1}

75 PERCEPTION_2        {if 151>@cell("row",TOP)#and#8192=@cell("row",BOTTOM)}{INPUT_4}{CARRY_1}
76                     {if 151>@cell("row",TOP)#and#8192>@cell("row",BOTTOM)}{INPUT_5}{CARRY_1}
77                     {if 151<@cell("row",TOP)#and#8192>>@cell("row",BOTTOM)}{INPUT_4}{CARRY_1}
78                     {if 151<@cell("row",TOP)#and#8192=@cell("row",BOTTOM)}{INPUT_6}{CARRY_1}

79 INPUT_4             {let CURRENT,@value(KBFR)}
80                     {if @iserr(CURRENT)<>0}{let CURRENT,KBFR}{branch INPUT4_1}
81 INPUT4_1            {menu}rp~
82                     {goto}EXT_CELL~
83                     {menu}rndCURRENT~
84                     {menu}rndTOP~
85                     {menu}rndBOTTOM~
86                     {menu}rndEXT_CELL~
87                     {u}{r}
88                     {return}

89 INPUT_5             {if @cell("row",TOP)+1=@cell("row",CURRENT)}{INPUT_4}{CARRY_1}
90                     {let CURRENT,@value(KBFR)}
91                     {if @iserr(CURRENT)<>0}{let CURRENT,KBFR}{branch INTERPOLATE_5}
92                     {INTERPOLATE_5}
93                     {goto}EXT_CELL~
94                     {menu}rndCURRENT~
95                     {menu}rndTOP~
```

```
 96                    {menu}mdBOTTOM~
 97                    {menu}mdHOKAN~
 98                    {menu}mdEXT_CELL~
 99                    {u}{r}
100                    {return}

101 INTERPOLATE_5      {menu}mcHOKAN~{bs}{down};{end}{down}~{up}~
102                    {menu}ruHOKAN~
103                    {recalc COLCAL1_2}
104                    {let HOKAN_7,COLCAL_2&+"148":value}
105                    {menu}c
106                    $A$148
107                    ~HOKAN~
108                    {menu}rpCURRENT~
109                    {menu}mpHOKAN~
110                    {return}

111 INPUT_6            {if @cell("row",TOP)+1=@cell("row",CURRENT)}{INPUT_4}{CARRY_1}
112                    {let CURRENT,@value(KBFR)}
113                    {if @isert(CURRENT)<>0}{let CURRENT,KBFR}{branch INTERPOLATE_6}
114                    {INTERPOLATE_6}
115                    {goto}EXT_CELL~
116                    {menu}mdCURRENT~
117                    {menu}mdTOP~
118                    {menu}mdBOTTOM~
119                    {menu}mdHOKAN~
120                    {menu}mdEXT_CELL~
121                    {u}{r}
122                    {return}

123 INTERPOLATE_6      {menu}mcHOKAN~{bs}{up};{end}{up}{down}~
124                    {menu}ruHOKAN~
```

Kumagai, MD       CMFCS (original for a C/S system)

125  {recalc COLCAL1_2}
126  {let HOKAN_6,COLCAL_2&+"148":value}
127  (menu)c
128  SE$1-t8
129  ~HOKAN~
130  (menu)rpCURRENT~
131  (menu)rpHOKAN~
132  {return}

CMFCS (new version for a C/S system)

The program list of the Computed Medical File and Chart System
(for Client Server System)
version 2.1 (new version)

Yasuo Kumagai, M.D.
January 4, 1995

*directory table*

| DIRECTORY | no_1 | no_2 | no_3 | no_4 |
|---|---|---|---|---|
| | A:\DATA\CMF | A:\DATA\CMF | A:\DATA\CMF | A:\DATA\CMFCS\NURSE |
| FILE_NAME | LABO_DAT | UV_DIET | DRUGS | |
| CONDITION | COND_1 | COND_1 | COND_1 | |
| OUTPUT | OUT_1 | OUT_2 | OUT_3 | |

*date calculation table*

| DAY_CTR | 0 |
|---|---|
| FIRST_DATE | 01/01/94 |
| START_DATE | 04/01/94 |
| DATA_DATE | 04/01/94 |
| TODAY | 30/01/94 |
| DATE_DIF | 3 |

| KBFR | 267 | SWITCH_1 | ERASE_1 |
|---|---|---|---|

| COLCAL_1 | $A$1 |
| COLCAL_2 | $A$5 |

```
1  DB_CHANGE (\C)  {menu}wgpd
2                  {menu}wgn1~
3                  {goto}DIR_TABLE~
4  DBCHANGE_1      {r}
5                  {if @cellpointer("type")="b"}{RESET_1}{quit}
6                  {menu}mcDIR_TEMP~~{d}
7                  {menu}mcFN_TEMP~~{d}
8                  {menu}mcCOND_TEMP~~{d}
9                  {menu}mcOUT_TEMP~~
10                 {let DIRECTRY,DIR_TEMP}
11                 {let FILE_1,FN_TEMP}
```

Kumagai, MD   CMFCS (new version for a C/S system)   - 2 -

```
12      {let FILE_2,FN_TEMP}
13      {let CONDITION,COND_TEMP}
14      {let OUTPUT,OUT_TEMP}
15      {menu}mdFN_TEMP~
16      {menu}mdCOND_TEMP~
17      {menu}mdOUT_TEMP~
18      {CONNECT}

19 RESET_1
20      {let DAY_CTR,0}
21      {let START_DATE,TODAY}
22      {menu}reDIRECTRY~
23      {menu}reFILE_1~
24      {menu}reFILE_2~
25      {menu}reCONDITION~
26      {menu}reOUTPUT~
27      {menu}wgpc
28      {menu}fsb~
        {return}

29 CONNECT
30      {onerror CONNECT_1}
31      {menu}dcv~{esc}
32      A:\DATA\CMFCS\LABO
33      ~{esc}
34      LABO_DAT
        ~q
35 CONNECT_1
36      {menu}dqi
        LABO_DAT
37      ~
38      COND_1
39      ~q
40      OUT_1
41      ~q
42      {LOOP}
43      {return}
```

CMFCS (new version for a C/S system)

Kumagai, MD                                                                                                  - 3 -

```
44 LOOP        {if DAY_CTR>TODAY-START_DATE}{RESET_2}{DBCHANGE_1}
45             {EXTRACT}

46 RESET_2     {goto}DIR_TEMP~
47             {menu}mdDIR_TEMP~
48             {let DAY_CTR,0}
49             {return}

50 EXTRACT     {let DAY_CTR,DAY_CTR+1}
51             {menu}rvDATA_DATE~COND_DATE~
52             {menu}dqe~q
53             {CARRY}

54 CARRY       {goto}OUT_1~
55 CARRY_1     {if @cellpointer("type")="b"}{u}{r}{CARRY_1}
56             {d}
57             {if @cellpointer("type")="b"}{u}{r}{CARRY_1}
58             {if @cellpointer("contents")=0}{u}{r}{CARRY_1}
59             {menu}mcEXT_CELL~
60             {menu}cEXT_CELL~KBFR~
61             {d 9+DATE_DIF}
62             {PDIC_4}

63 PDIC_4      {menu}rfg~
64             {if @cellpointer("type")<>"b"}{CARRY_1}
65             {NAMING}
```

Kumagai, MD                CMFCS (new version for a C/S system)                -4-

66          {PERCEPTION_4}

67 PERCEPTION_4
68          {if 151>@cell("row",TOP)#and#8192=@cell("row",BOTTOM)}{INPUT_4}{CARRY_1}
69          {if 151<=@cell("row",TOP)#and#8192=@cell("row",BOTTOM)}{INPUT_6}{CARRY_1}
            {CARRY_1}

70 INPUT_4  {let CURRENT,@value(KBFR)}
71          {if @isrrr(CURRENT)<>0}{let CURRENT,KBFR}{INPUT4_1}
72 INPUT4_1 {menu}rp~
73          {goto}EXT_CELL~
74          {menu}mdCURRENT~
75          {menu}mdTOP~
76          {menu}mdBOTTOM~
77          {menu}mdEXT_CELL~
78          {u}{r}
79          {return}

80 INPUT_6  {if @cell("row",TOP)+1=@cell("row",CURRENT)}{INPUT_4}{CARRY_1}
81          {if @length(KBFR)<1}{CARRY_1}
82          {let CURRENT,@value(KBFR)}
83          {if @isrrr(CURRENT)<>0}{let CURRENT,KBFR}{branch INTERPOLATE_6}
84          {INTERPOLATE_6}
85          {menu}rpORIGIN~
86          {menu}rpCURRENT~
87          {menu}rpHOKAN~
88          {goto}EXT_CELL~
89          {menu}mdORIGIN~
90          {menu}mdCURRENT~
91          {menu}mdHOKAN~
92          {menu}mdTOP~
93          {menu}mdBOTTOM~
94          {menu}mdEXT_CELL~

'. Kumagai, MD                                   CMFCS (new version for a C/S system)                    - 5 -

```
 95         {u}{:}
 96         {return}

97 INTERPOLATE_6  {menu}mcHOKAN~{bs}{up}{end}{up}{down}~
 98         {menu}ruHOKAN~
 99         {recalc COLCAL1_2}
100         {let HOKAN_6,COLCAL_2&+"148":value}
101         {goto}
102         $ES148
103         ~
104         {menu}mcORIGIN~
105         {menu}ruORIGIN~
106         {edit}{home}{del}~
107         {menu}cORIGIN~HOKAN~
108         {goto}ORIGIN~
109         {edit}{home}~
110         {goto}CURRENT~
111         {menu}rvHOKAN~HOKAN~
112         {return}
```

CMFCS (original for a manual system)

The program list of the Computed Medical File and Chart System
(for Manual System)
version 1.1 (orginal version)

Yasuo Kumagai, M.D.
January 4, 1995

SWITCH_1 [ERASE 4]    COLCAL_1 [$A$1]
                      COLCAL_2 [$A$]

[1.25]

KBFR

1 PDIC_1 (1D)
2           {COVER}
3           {menu}wgpc
4           {menu}wgn1~
5           {menu}rfg~
6           {menu}ruKBFR~
7           {NAMING}
            {PERCEPTION_1}

8 COVER
9           {indicate executing}
10          {paneloff}
11          {windowsoff}
            {return}

12 NAMING   {menu}mcCURRENT~
13          {menu}ruCURRENT~
14          {menu}reCURRENT~
15          {end}{down}
16          {menu}mcBOTTOM~
17          {goto}CURRENT~

/. Kumagai, MD             CMFCS (original for a manual system)                                        - 2 -

18      {end}{up}
19      {menu}rncTOP~
20      {goto}CURRENT~
21      {return}

22 PERCEPTION_1   {if 151=@cell("row",TOP)#and#@cell("type",TOP)="b"#and#8192=@cell("row",BOTTOM)}{let SWITCH_1,"ERASE_1"}{DSP_CTL}{UNCOVER}{INPUT_1}
23      {if 151=@cell("row",TOP)#and#8192>@cell("row",BOTTOM)}{let SWITCH_1,"ERASE_2"}{DSP_CTL}{UNCOVER}{INPUT_2}
24      {if 151<@cell("row",TOP)#and#8192>@cell("row",BOTTOM)}{let SWITCH_1,"ERASE_3"}{DSP_CTL}{UNCOVER}{INPUT_1}
25      {let SWITCH_1,"ERASE_4"}
26      {DSP_CTL}
27      {UNCOVER}
28      {INPUT_3}

29 DSP_CTL   {if @cell("row",CURRENT)<163#and#@cell("col",CURRENT)<10}{home}{goto}CURRENT~{return}
30      {if @cell("row",CURRENT)<163#and#@cell("col",CURRENT)>11}{up @cell("row",CURRENT)-151}{left 5}{goto}CURRENT~{return}
31      {if @cell("row",CURRENT)>164#and#@cell("col",CURRENT)<10}{up 13}{left @cell("col",CURRENT)-3}{goto}CURRENT~{return}
32      {up 13}{left 5}{goto}CURRENT~{return}

29 UNCOVER   {indicate}
30      {panelon}
31      {windowson}
32      {return}

33 INPUT_1   {getlabel Please input the data ,KBFR}
34      {COVER}
35      {if @length(KBFR)<1}{dispatch SWITCH_1}
36      {let CURRENT,@value(KBFR)}
37      {if @iserr(CURRENT)<>0}{let CURRENT,KBFR}{branch INPUT1_1}
38 INPUT1_1   {DSP_CTL}
39      {menu}rp~
40      {STOP}

CMFCS (original for a manual system)

- 3 -

```
41 STOP          {goto}CURRENT~
42               {menu}rpCURRENT~
43               {menu}rndCURRENT~
44               {menu}rndTOP~
45               {menu}rndBOTTOM~
46               {UNCOVER}
47               {quit}

48 INPUT_2       {if @cell("row",CURRENT)+1=@cell("row",BOTTOM)}{let SWITCH_1, "ERASE_1"}{DSP_CTL}{UNCOVER}{INPUT_1}
49               {getlabel Please input the data, KBFR}
50               {COVER}
51               {if @length(KBFR)<1}{dispatch SWITCH_1}
52               {let CURRENT,@value(KBFR)}
53               {if @iserr(CURRENT)<>0}{let CURRENT,KBFR}{branch INTERPOLATE_U}
54               {INTERPOLATE_2}
55               {KEISAN}
56               {UNCOVER}
57               {quit}

58 INTERPOLATE_2 {menu}mcHOKAN~{bs}{down};{end}{down}{up}~
59               {menu}ruHOKAN~
60               {recalc COLCAL1_2}
61               {let HOKAN_4,COLCAL_2&+"148",value}
62               {menu}c
63               $D$148
64               ~HOKAN~
65               {DSP_CTL}
66               {menu}rpCURRENT~
67               {menu}rpHOKAN~
68               {menu}rndCURRENT~
69               {menu}rndTOP~
70               {menu}rndBOTTOM~
71               {menu}rndHOKAN~
72               {return}
```

Kumagai, MD CMFCS (original for a manual system)

```
73 KEISAN      {menu}wgri50~
74             {calc}
75             {calc}
76             {calc}
77             {menu}wgri1~
78             {return}

79 INPUT_3     {if @cell("row",TOP)+1=@cell("row",CURRENT)}{let SWITCH_1,"ERASE_1"}{DSP_CTL}{UNCOVER}{INPUT_1}
80             {getlabel Please input the data ,KBFR}
81             {COVER}
82             {if @length(KBFR)<1}{dispatch SWITCH_1}
83             {let CURRENT,@value(KBFR)}
84             {if @iserr(CURRENT)<>0}{let CURRENT,KBFR}{branch INPUT3_1}
85             {INTERPOLATE_3}
86             {KEISAN}
87             {UNCOVER}
88             {quit}

89 INTERPOLATE_3  {menu}mcHOKAN~{bs}{up}{end}{up}{down}~
90             {menu}nuHOKAN~
91             {recalc COLCAL1_2}
92             {let HOKAN_3,COLCAL_2&+"148":value}
93             {menu}c
94             SES148
95             ~HOKAN~
96             {DSP_CTL}
97             {menu}rpCURRENT~
98             {menu}rpHOKAN~
99             {menu}mdCURRENT~
100            {menu}mdTOP~
101            {menu}mdBOTTOM~
102            {menu}mdHOKAN~
103            {return}
```

Kumagai, MD  CMFCS (original for a manual system)  - 5 -

```
104 ERASE_1      {menu}reCURRENT~
105              {DSP_CTL}
106              {STOP}

107 ERASE_2      {menu}reCURRENT~
108 ERASE2_1     {down}
109              {if @cellpointer("format")<>"H"}{DSP_CTL}{STOP}
110              {menu}ru~
111              {menu}re~
112              {menu}rfg~
113              {menu}rp~
114              {branch ERASE2_1}

115 ERASE_3      {recalc COLCAL1_2}
116              {let HOKAN_5,COLCAL_2&+"148",value}
117              {menu}c
118              $DS148
119              ~
120              {KEISAN}
121              {STOP}

122 ERASE_4      {menu}reCURRENT~
123 ERASE4_1     {up}
124              {if @CELLPOINTER("format")<>"H"}{DSP_CTL}{STOP}
125              {menu}ru~
126              {menu}re~
127              {menu}rfg~
128              {menu}rp~
129              {branch ERASE4_1}
```

Kumagai, MD

CMFCS (new version for a manual system)

The program list of the Computed Medical File and Chart System
(for Manual System)
version 2.1 (new version)

Yasuo Kumagai, M.D.
January 4, 1995

SWITCH_1 [ERASE_1]    COLCAL_1 [$A$1]
                      COLCAL_2 [$A$]

KBFR                [267]

1 PDIC_3 (D)        {COVER}
2                   {menu}wgpe~
3                   {menu}wgr1~
4                   {if @cellpointer("type")<>"b"}{quit}
5                   {NAMING}
6                   {PERCEPTION_3}
7                   {INPUT_1}

8 COVER             {indicate executing}
9                   {paneloff}
10                  {windowsoff}
11                  {return}

12 NAMING           {menu}mcCURRENT~
13                  {home}
14                  {goto}CURRENT~
15                  {menu}rfg~
16                  {menu}ruKBFR~
17                  {menu}ruCURRENT~

CMFCS (new version for a manual system)

```
18      {menu}reCURRENT~
19      {end}{down}
20      {menu}mcBOTTOM~
21      {goto}CURRENT~
22      {end}{up}
23      {menu}mcTOP~
24      {goto}CURRENT~
25      {return}

26 PERCEPTION_3
27      {if 151=@cell("row",TOP)#and#@cell("type",TOP)="b"#and#8192=@cell("row",BOTTOM)}{DSP_CTL}{UNCOVER}{INPUT_1}
        {if 151=@cell("row",TOP)#and#@cell("type",TOP)<>"b"#and#8192=@cell("row",BOTTOM)}{DSP_CTL}{UNCOVER}{INPUT_3}
28      {if 151<@cell("row",TOP)#and#8192=@cell("row",BOTTOM)}{DSP_CTL}{UNCOVER}{INPUT_3}

29 DSP_CTL
        {if @cell("row",CURRENT)<163#and#@cell("col",CURRENT)<10}{home}{goto}CURRENT~{return}
30      {if @cell("row",CURRENT)<163#and#@cell("col",CURRENT)>11}{up @cell("row",CURRENT)-151}{left 5}{goto}CURRENT~{return}
31      {if @cell("row",CURRENT)>164#and#@cell("col",CURRENT)<10}{up 13}{left @cell("col",CURRENT)-3}{goto}CURRENT~{return}
32      {up 13}{left 5}{goto}CURRENT~{return}

33 UNCOVER
34      {indicate}
35      {panelon}
        {windowson}
36      {return}

37 INPUT_1
        {getlabel Please input new data, ,KBFR}
38      {COVER}
39      {if @length(KBFR)<1}{STOP}
40      {let CURRENT,@value(KBFR)}
41      {if @isert(CURRENT)<>0}{let CURRENT,KBFR}{branch INPUT1_1}
42      {DSP_CTL}
43 INPUT1_1
        {menu}rp~
44      {menu}mdCURRENT~
45      {menu}mdTOP~
```

Kumagai, MD                                          CMFCS (new version for a manual system)

- 3 -

46        {menu}mdBOTTOM~
47        {UNCOVER}
48        {quit}

49 INPUT_3  {if @cell("row",TOP)+1=@cell("row",CURRENT)}{INPUT_1}
50          {getlabel Please input new data, ;KBFR}
51          {COVER}
52          {if @length(KBFR)<1}{STOP}
53          {let CURRENT,@value(KBFR)}
54          {if @iserr(CURRENT)<>0}{let CURRENT,KBFR}{branch INTERPOLATE_3}
55          {INTERPOLATE_3}
56          {menu}rpORIGIN~
57          {menu}rpCURRENT~
58          {menu}rpHOKAN~
59          {menu}mdORIGIN~
60          {menu}mdHOKAN~
61          {menu}mdCURRENT~
62          {menu}mdTOP~
63          {menu}mdBOTTOM~
64          {UNCOVER}
65          {quit}

66 INTERPOLATE_3  {menu}mcHOKAN~{bs}{up}{end}{up}{down}~
67                {menu}nuHOKAN~
68                {recalc COLCAL1_2}
69                {let HOKAN_3,COLCAL_2&+"148":value}
70                {goto}
71                $E$148
72                ~
73                {menu}mcORIGIN~
74                {menu}nuORIGIN~
75                {edit}{home}{del}~
76                {menu}cORIGIN~HOKAN~
77                {goto}ORIGIN~
78                {edit}{home}~
79                {DSP_CTL}

CMFCS (new version for a manual system)      - 4 -

Kumagai, MD

80  {home}
81  {goto}IV8192~
82  {goto}CURRENT~
83  {menu}rvHOKAN~HOKAN~

Kumagai, M.D.                                                          CMFCS (ver. 3.0 for manual system)

The program list of the Computed Medical File and Chart System
(for Manual System)
version 3.0

Yasuo Kumagai, M.D.
July 13, 1995

KBFR                    SWITCH_1 [ERASE_1]           CALCOL_1 [SAF$15]
                                                     CALCOL_2 [SAF]

```
1  {COVER}
2  {menu}wgrl~
3  {menu}meCURRENT~
4  {menu}rfr~
5  {menu}ruKBFR~
6  {menu}roCURRENT~
7  {menu}reCURRENT~
8  {end}{down}
9  {menu}rseBOTTOM~
0  {goto}CURRENT~
1  {end}{up}
2  {menu}rseTOP~
3  {goto}CURRENT~
4  {if 1$1=@cell("row",TOP)#and#@cell("type",TOP)="b"#and#8192=@cell("row",BOTTOM)}{let SWITCH_1,"ERASE_1"}{DSP_CTL}{UNCOVER}{INPUT_1}
5  {if 1$1=@cell("row",TOP)#and#@cell("type",TOP)<>"b"#and#8192=@cell("row",BOTTOM)}{let SWITCH_1,"ERASE_3"}{DSP_CTL}{UNCOVER}{INPUT_3}
6  {if 1$1=@cell("row",TOP)#and#8192>@cell("row",BOTTOM)#and#@cell("format",BOTTOM)<>"H"}{let SWITCH_1,"ERASE_2"}{DSP_CTL}{UNCOVER}{INPUT_2}
7  {if 1$1=@cell("row",TOP)#and#8192>@cell("row",BOTTOM)#and#@cell("format",BOTTOM)="H"}{let SWITCH_1,"ERASE4_3C"}
8  {if @cell("row",TOP)+1=@cell("row",CURRENT)#and#@cell("row",BOTTOM)+1=@cell("row",CURRENT)#and#@cell("row",TOP)<>"H"}{let SWITCH_1,"ERASE4_2"}{DSP_CTL}{UNCOVER}{INPUT_4}
9  {if @cell("row",TOP)+1=@cell("row",CURRENT)#and#@cell("row",BOTTOM)+1=@cell("row",CURRENT)#and#@cell("format",TOP)="H"}{let SWITCH_1,"ERASE_4"}{DSP_CTL}{UNCOVER}{INPUT_4}
0  {if @cell("row",TOP)+1=@cell("row",CURRENT)#and#@cell("row",BOTTOM)}{let SWITCH_1,"ERASE_3"}{DSP_CTL}{UNCOVER}{INPUT_4B}
1  {if 1$1=@cell("row",TOP)#and#8192=@cell("row",BOTTOM)}{let SWITCH_1,"ERASE_3"}{DSP_CTL}{UNCOVER}{INPUT_3}
2  {INPUT_1}
```

Kumagai, M.D.  CMFCS (ver. 3.0 for manual system)

```
23 DSP_CTL   {if @cell("row",CURRENT)<163#and#@cell("col",CURRENT)<38} {home} {goto}CURRENT~{return}
24           {if @cell("row",CURRENT)<163#and#@cell("col",CURRENT)>39} {up @cell("row",CURRENT)-151} {left 5} {goto}CURRENT~{return}
25           {if @cell("row",CURRENT)>164#and#@cell("col",CURRENT)<38} {up 13} {left @cell("col",CURRENT)-3} {goto}CURRENT~{return}
26           {up 13} {left 5} {goto}CURRENT~{return}

27 COVER     {indicate executing}
28           {paneloff}
29           {windowsoff}
30           {return}

31 UNCOVER   {indicate}
32           {panelon}
33           {windowson}
34           {return}

35 STOP      {goto}CURRENT~
36           {menu}rpCURRENT~
37           {menu}mdCURRENT~
38           {menu}mdTOP~
39           {menu}mdBOTTOM~
40           {UNCOVER}
41           {quit}

42 INPUT_1   {getlabel Please input new data, ;KBFR}
43           {COVER}
44           {if @length(KBFR)=1} {dispatch SWITCH_1}
45           {let CURRENT,@value(KBFR)}
46           {if @ibett(CURRENT)<>0} {let CURRENT,KBFR} {branch INPUT1_1}
47 INPUT1_1  {menu}rp~
48           {menu}mdTOP~
49           {menu}mdBOTTOM~
50           {DSP_CTL}
51           {menu}mdCURRENT~
52           {UNCOVER}
53           {quit}
```

Kumagai, M.D.  CMFCS (ver. 3.0 for manual system)

```
54 INPUT_2    {if @cell("row",CURRENT)+1=@cell("row",BOTTOM)} {INPUT_1}
55            {getlabel Please input new data. ,KBFR}
56            {COVER}
57            {if @length(KBFR)<1} {dispatch SWITCH_1}
58            {let CURRENT,@value(KBFR)}
59            {if @insert(CURRENT,KBFR)<0} {let CURRENT,KBFR} {branch INPUT2_1}
60 INPUT_1    {menu}mcHOKAN~{bs} {down}. {end} {down} {up}~
61            {menu}ruHOKAN~
62            {resale CALCOL1_2}
63            {let HOKAN_2,CALCOL_2&+"146",value}
64            {goto}
65            SAF146
66            ~
67            {menu}mcORIGIN~
68            {menu}mORIGIN~
69            {edit} {home} {del}~
70            {menu}cORIGIN~HOKAN~
71            {goto}ORIGIN~
72            {edit} {home}~
73            {goto}IV8192~
74            {home}
75            {goto}CURRENT~
76            {menu}rvHOKAN~HOKAN~
77            {menu}rpORIGIN~
78            {menu}rpCURRENT~
79            {menu}rpHOKAN~
80            {menu}mdORIGIN~
81            {menu}mdHOKAN~
82            {menu}mdTOP~
83            {menu}mdBOTTOM~
84            {DSP_CTL}
85            {menu}mdCURRENT~
86            {UNCOVER}
87            {quit}
```

```
Kumagai, M.D.                                                    CMFCS (ver. 3.0 for manual system)

28  INPUT_3     {if @cell("row",TOP)+1=@cell("row",CURRENT)}{INPUT_1}
29              {getlabel Please input new data. ;KBFR}
30              {COVER}
31              {if @length(KBFR)<1}{dispatch SWITCH_1}
32              {let CURRENT,@value(KBFR)}
33              {if @iserr(CURRENT)<>0}{let CURRENT,KBFR}{branch INPUT3_1}
34  INPUT3_1    {menu}mcHOKAN~{bs}{up}{end}{up}{down}~
35              {menu}nLHOKAN~
36              {recalc CALCOL1_2}
37              {let HOKAN_3,CALCOL_2&+"148";value}
38              {goto}
39              SAG1-48
40              ~
31              {menu}mcORIGIN~
32              {menu}nrORIGIN~
33              {edit}{home}{del}~
34              {menu}cORIGIN~HOKAN~
35              {goto}ORIGIN~
36              {edit}{home}~
37              {goto}IV8192~
08              {home}
09              {goto}CURRENT~
10              {menu}rvHOKAN~HOKAN~
11              {menu}rpORIGIN~
12              {menu}rpCURRENT~
13              {menu}rpHOKAN~
14              {menu}mdORIGIN~
15              {menu}mdHOKAN~
16              {menu}mdTOP~
17              {menu}mdBOTTOM~
18              {DSP_CTL}
19              {menu}mdCURRENT~
20              {UNCOVER}
21              {quit}
```

```
Imagau, M.D.                                         CMFCS (ver. 3.0 for manual system)

2 INPUT_4        {COVER};
 3                {menu}mdTOP~
 4                {menu}mdBOTTOM~
 5 INPUT4_1       {up}
 6                {if @CELLPOINTER("format")<>"H"} {menu}mcTOP~~{INPUT4_2}
 7                {menu}ru~
 8                {menu}re~
 9                {menu}rd~
 0                {branch INPUT4_1}

1 INPUT4_2       {goto}CURRENT~
 2                {UNCOVER}
 3                {if @cell("row",TOP)+1=@cell("row",CURRENT)} {INPUT4_3B}
 4                {getlabel Please input new data. ,KBFR}
 5                {COVER}
 6                {if @length(KBFR)<1} {dispatch SWITCH_1}
 7                {let CURRENT,@value(KBFR)}
 8                {menu}mcHOKAN~{bs} {up}.{end} {up} {down}~
 9                {menu}ruHOKAN~
 0                {recalc CALCOL_2}
 1                {let HOKAN_4A,CALCOL_2&+"148"value}
 2                {goto}
 3                SAGI-8
 4                ~
 5                {menu}mcORIGIN~~
 6                {menu}ruORIGIN~
 7                {edit} {home} {del}~
 8                {menu}cORIGIN~HOKAN~
 9                {goto}ORIGIN~
 0                {edit} {home}~
 1                {goto}IV8192~
 2                {home}
 3                {goto}CURRENT~
 4                {menu}rvHOKAN~HOKAN~
 5                {menu}rpORIGIN~
 6                {menu}rpCURRENT~
 7                {menu}rpHOKAN~
 8                {menu}mdORIGIN~
 9                {menu}mdHOKAN~
 0                {DSP_CTL}
 1                {INPUT4_3}
```

Kumagai, M.D.                                                                CMFCS (ver. 3.0 for manual system)

```
52 INPUT_4B         {COVER}
53                  {menu}mdTOP~
54 INPUT4B_1        {up}
55                  {if @CELLPOINTER("format")<>"H"}{menu}mcTOP~~{INPUT4B_2}
56                  {menu}ru~
57                  {menu}re~
58                  {menu}rd~
59                  {branch INPUT4B_1}

70 INPUT4B_2        {goto}CURRENT~
71                  {UNCOVER}
72                  {if @cell("row",TOP)+1=@cell("row",CURRENT)}{STOP}
73                  {getlabel Please input new data. ;KBFR}
74                  {COVER}
75                  {if @length(KBFR)<1}{dispatch SWITCH_1}
76                  {let CURRENT,@value(KBFR)}
77                  {menu}mcHOKAN~{bs}{up}.{end}{up}{down}~
78                  {menu}ruHOKAN~
79                  {recalc CALCOL_2}
80                  {let HOKAN_4B,CALCOL_2&+"148".value}
81                  {goto}
82                  \AG148
83                  ~
84                  {menu}mcORIGIN~
85                  {menu}ruORIGIN~
86                  {edit}{home}{del}~
87                  {menu}cORIGIN~HOKAN~
88                  {goto}ORIGIN~
89                  {edit}{home}~
90                  {goto}IV8192~
91                  {home}
92                  {goto}CURRENT~
93                  {menu}rvtHOKAN~HOKAN~
94                  {menu}rpORIGIN~
95                  {menu}rpCURRENT~
96                  {menu}rpHOKAN~
97                  {menu}rndORIGIN~
98                  {menu}rndHOKAN~
99                  {DSP_CTL}
00                  {STOP}
```

Kumagai, M.D.                                        CMFCS (ver. 3.0 for manual system)

```
01 INPUT4_3    {COVER}
02             {goto}CURRENT~
03 INPUT4_4    {down}
04             {if @CELLPOINTER("format")<>"H"}{menu}mcBOTTOM~~{INPUT4_5}
05             {menu}ru~
06             {menu}re~
07             {menu}rf~
08             {branch INPUT4_4}

09 INPUT4_3C   {COVER}
10             {menu}mcBOTTOM~
11             {INPUT4_3B}

12 INPUT4_3B   {COVER}
13             {goto}CURRENT~
14 INPUT4_4B   {down}
15             {if @CELLPOINTER("format")<>"H"}{menu}mcBOTTOM~~{INPUT4_5B}
16             {menu}ru~
17             {menu}re~
18             {menu}rf~
19             {branch INPUT4_4B}

20 INPUT4_5B   {getlabel Please input new data. ,KBFR}
21             {COVER}
22             {if @length(KBFR)>1}{dispatch SWITCH_1}
23             {let CURRENT,@value(KBFR)}
24             {INPUT4_5}
```

Kumagai, M.D.  CMFCS (ver. 3.0 for manual system)

```
25 INPUT4_5  {goto}CURRENT~
26           {if @cell("row",CURRENT)+1=@cell("row",BOTTOM)}{STOP}
27           {menu}rncHOKAN~{bs}{down}.{end}{down}{up}~
28           {menu}rnHOKAN~
29           {recalc CALCOL_2}
30           {let HOKAN_4C,CALCOL_2&+"146*value}
31           {goto}
32           SAG146
33           ~
34           {menu}rncORIGIN~
35           {menu}rnORIGIN~
36           {edit}{home}{del}~
37           {menu}cORIGIN~HOKAN~
38           {goto}ORIGIN~
39           {edit}{home}~
40           {goto}IV8192~
41           {home}
42           {goto}CURRENT~
43           {menu}rHOKAN~HOKAN~
44           {menu}rpORIGIN~
45           {menu}rpCURRENT~
46           {menu}rpHOKAN~
47           {menu}rdORIGIN~
48           {menu}rdHOKAN~
49           {menu}rdTOP~
50           {menu}rdBOTTOM~
51           {DSP_CTL}
52           {menu}rdCURRENT~
53           {UNCOVER}
54           {quit}
```

CMFCS (ver. 3.0 for manual system)

Funagai, M.D.                                                                          - 9 -

```
5 ERASE_1      {menu}reCURRENT~
                {DSP_CTL}
                {STOP}

3 ERASE_2      {COVER}
                {menu}reCURRENT~
9 ERASE2_1     {down}
1              {if @cellpointer("format")<>"H"}{DSP_CTL}{STOP}
2              {menu}ru~
3              {menu}re~
4              {menu}rf~
5              {menu}rp~
6              {branch ERASE2_1}

7 ERASE_3      {COVER}
8              {menu}reCURRENT~
9 ERASE3_1     {up}
0              {if @CELLPOINTER("format")<>"H"}{DSP_CTL}{STOP}
1              {menu}ru~
2              {menu}re~
3              {menu}rf~
4              {menu}rp~
5              {branch ERASE3_1}

6 ERASE_4      {COVER}
7              {goto}CURRENT~
8 ERASE4_1     {down}
9              {if @CELLPOINTER("format")<>"H"; {menu}rucBOTTOM~{ERASE4_2}
0              {menu}ru~
1              {menu}re~
2              {menu}rf~
3              {branch ERASE4_1}
```

Kumagai, M.D.

CMFCS (ver. 3.0 for manual system)

```
4  ERASE4_2  {menu}mcHOKAN~{bs}{up}{end}{up}{down}~
85         {menu}ruHOKAN~
86         {recalc CALCOL1_2}
87         {let HOKAN_5,CALCOL_2&+"147";value}
88         {goto}
89         SAG147
90         ~
91         {menu}rucORIGIN~
92         {menu}ruORIGIN~
93         {edit}{home};{del}~
94         {menu}cORIGIN~HOKAN~
95         {goto}ORIGIN~
96         {edit}{home}~
97         {goto}IV8192~
98         {home}
99         {goto}CURRENT~
00         {menu}rvHOKAN~HOKAN~
01         {menu}rpORIGIN~
02         {menu}rpCURRENT~
03         {menu}rpHOKAN~
04         {menu}mdORIGIN~
05         {menu}mdHOKAN~
06         {DSP_CTL}
07         {STOP}
```

What is claimed is:

1. A method of producing medical charts comprising the steps of:

monitoring conditions of a patient and taking measurements reflecting those patient conditions;

entering datum resulting from said measurements into a buffer in a digital computer;

determining the chronological position in a row and column structure where said entered datum should be stored;

determining the position of a previously entered piece of datum located in the same column as said entered datum;

interpolating data located in the rows between said entered datum and said previously entered piece of datum by summing the data in the row above and below the particular row that is being interpolated, dividing that sum by two, and storing the calculated value in the row that is being interpolated; and displaying on said digital computer's output a medical record containing said entered datum, said previously entered piece of datum, and said interpolated data.

2. The method of producing medical charts according to claim 1, further comprising the multiple execution of said interpolation step so as to obtain interpolated values which approach a straight line between said entered piece of datum and said previously entered piece of datum.

3. The method of producing medical charts according to claim 1, wherein said previously entered piece of datum is the closest piece of datum to said entered datum located above said entered datum.

4. The method of producing medical charts according to claim 3, further comprising the steps of determining the position of a second previously entered piece of datum located in the same column and a row disposed below said entered datum, and interpolating data located in the rows between said entered datum and said second previously entered datum.

5. The method of producing medical charts according to claim 4, wherein said second previously entered piece of datum is the closest piece of datum to said entered datum located below said entered datum.

6. The method of producing medical charts according to claim 1, wherein said row and column structure comprises a plurality of rows and columns.

7. The method of producing medical charts according to claim 6, wherein said rows designate a particular period in time, said columns designate a particular patient condition that is being monitored, and said entered data and said previously entered data are measurements of said patient conditions.

8. The method of producing medical charts according to claim 7, wherein said patient conditions are selected from the group comprising blood pressure, pulse rate, body temperature and urine volume.

9. The method of producing medical charts according to claim 1, wherein said entered datum and said previously entered data is retrieved from a database by a client-server program.

10. The method of producing medical charts according to claim 9, wherein said database is identified by a directory table and matching data items in a predetermined row of said problem oriented medical record.

11. The method of producing medical charts according to claim 1, wherein said row and column structure is embodied in a problem oriented medical record and said problem oriented medical record is displayed on a computer screen display.

12. The method of producing medical charts according to claim 11, wherein said problem oriented medical records are displayed in a multiple fashion.

13. The method of producing medical charts according to claim 12, wherein said data from said problem oriented medical record is displayed in graphic form on a medical chart.

14. The method of producing medical charts according to claim 12, wherein a plurality of charts are overlapped allowing for the comparison of therapeutic, clinical, real and interpolated data collected at irregular intervals for multiple patients.

15. The method of producing medical charts according to claim 1, wherein said row and column structure represents a standardized time scale for the scheduled recording of data.

16. A method of producing medical charts according to claim 1, wherein multiple patient conditions are monitored, collected and recorded for multiple patients, and said multiple patient conditions placed on the same graph to allow ease of comparison in relation to each patient.

17. A method of producing medical charts according to claim 1, wherein multiple conditions for a patient are monitored and collected from different sources, and subsequently displayed on said medical record.

18. A method of producing medical charts comprising the steps of:

monitoring conditions of a patient and taking measurements reflecting those patient conditions;

entering datum resulting front said measurements into a buffer in a digital computer;

determining the chronological position in a row and column structure where said entered datum should be stored, said row and column struggle forming data cells;

determining the position of a previously entered piece of datum located in the same column as said entered datum;

interpolating data for said data cells located between said entered datum and said previously entered piece of datum where one or more of said data cells located between said entered datum and said previously entered piece of datum contain no data therein; and displaying on said digital computer's output a medical record containing said entered datum, said previously entered piece of datum, and said interpolated data.

19. A method of producing medical charts comprising the steps of:

monitoring conditions of a patient and taking measurements reflecting those patient conditions;

entering datum resulting from said measurements into a buffer in a digital computer;

determining the chronological position in a row and column structure where said entered datum should be stored;

determining the position of a previously entered piece of datum located in the same column as said entered datum;

interpolating data for the rows between said entered datum and said previously entered piece of datum by determining the difference of said entered datum and said previously entered piece of datum;

dividing said difference by the number of rows separating said entered datum and said previously entered datum to obtain a first result;

multiplying said first result by the row number for which the interpolation is taking place to obtain a second result, adding an intercept value to said second result to obtain an interpolated value, and displaying on said digital computer's output a medical record containing said entered datum, said previously entered piece of datum, and said interpolated value.

20. The method of producing medical charts according to either claims 1, 18 or 19, further comprising the steps of:

collecting a plurality of said medical charts from a plurality of said patients; and using said plurality of said medical charts in the comparison of said entered datum, said previously entered piece of datum, and said interpolated data among the plurality of said patients.

21. The method of producing medical charts according to claim 20, wherein said comparison is used in connection with an epidemiological study.

22. The method of producing medical charts according to claim 20, wherein said comparison is used in connection with a study on the effectiveness of a new drug.

* * * * *